US011747281B2

(12) United States Patent
Lee et al.

(10) Patent No.: US 11,747,281 B2
(45) Date of Patent: Sep. 5, 2023

(54) SPECTROSCOPIC APPARATUS AND SPECTROSCOPIC METHOD USING TIME RESOLVED CODING

(71) Applicant: ELECTRONICS AND TELECOMMUNICATIONS RESEARCH INSTITUTE, Daejeon (KR)

(72) Inventors: Won Kyoung Lee, Daejeon (KR); Hong-Seok Seo, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 124 days.

(21) Appl. No.: 17/618,205

(22) PCT Filed: Jul. 14, 2020

(86) PCT No.: PCT/KR2020/009244
§ 371 (c)(1),
(2) Date: Dec. 10, 2021

(87) PCT Pub. No.: WO2021/085801
PCT Pub. Date: May 6, 2021

(65) Prior Publication Data
US 2022/0163452 A1  May 26, 2022

(30) Foreign Application Priority Data
Oct. 29, 2019  (KR) .................. 10-2019-0135817

(51) Int. Cl.
*G01N 21/65* (2006.01)
*G01N 33/483* (2006.01)

(52) U.S. Cl.
CPC .......... *G01N 21/65* (2013.01); *G01N 33/483* (2013.01); *G01N 2201/06113* (2013.01)

(58) Field of Classification Search
None
See application file for complete search history.

(56) References Cited

U.S. PATENT DOCUMENTS 7,649,616 B2   1/2010   Michael et al.
9,207,408 B1  12/2015   Teodoro et al.
(Continued)

FOREIGN PATENT DOCUMENTS

| KR | 10-2018-0123867 A | 11/2018 | |
|----|-------------------|---------|---|
| WO | 2011/077203 A2 | 6/2011 | |
| WO | WO-2011077203 A2 * | 6/2011 | ........... A61B 5/0059 |

OTHER PUBLICATIONS

E.S. Fotso Guetue et al., "Nanosecond time resolved Raman spectroscopy for solving some Raman problems such as luminescence or thermal emission", Journal of Raman Spectroscopy, vol. 49, pp. 822-829, Feb. 14, 2018.

*Primary Examiner* — Tarifur R Chowdhury
*Assistant Examiner* — Roberto Fabian, Jr.
(74) *Attorney, Agent, or Firm* — Rabin & Berdo, P.C.

(57) ABSTRACT

Disclosed is a spectroscopic apparatus includes a laser irradiation device that receives an orthogonal code including a series of bits each having a first value or a second value, generates a control signal having a pulse that has a width shorter than a width of a bit section in the bit section corresponding to a bit having the first value, generates a pulsed laser beam having a pulse width shorter than the bit section using the pulse as a trigger, and irradiates an incident beam including the generated pulsed laser beam to a sample, and a detector that receives a detection signal generated from the sample and the orthogonal code, generates an orthogonal code signal of the same waveform as that of the incident beam, based on the orthogonal code, and demodu- (Continued)

lates a Raman signal, based on a correlation between the generated orthogonal code signal and the Raman signal.

15 Claims, 17 Drawing Sheets

(56) References Cited

U.S. PATENT DOCUMENTS

| | | |
|---|---|---|
| 10,345,243 B2 | 7/2019 | Lee et al. |
| 2005/0122570 A1 | 6/2005 | Chang et al. |
| 2005/0254047 A1* | 11/2005 | Brady .................. G01J 3/10 |
| | | 356/301 |
| 2009/0274470 A1 | 11/2009 | Koshino et al. |
| 2011/0261354 A1 | 10/2011 | Sinfield et al. |
| 2012/0203114 A1 | 8/2012 | Bechtel et al. |
| 2014/0293279 A1* | 10/2014 | Kwok .................. G01N 21/65 |
| | | 356/301 |
| 2015/0133787 A1 | 5/2015 | Wegner |
| 2018/0143296 A1 | 5/2018 | Lee et al. |
| 2018/0328851 A1 | 11/2018 | Lee et al. |
| 2020/0177298 A1 | 6/2020 | Myung et al. |

\* cited by examiner

SPECTROSCOPIC APPARATUS AND SPECTROSCOPIC METHOD USING TIME RESOLVED CODING

TECHNICAL FIELD

The inventive concept relates to a spectroscopic apparatus and a spectroscopic method, and more particularly, relates to a spectroscopic apparatus and a spectroscopic method that analyze biomolecules using a time resolved coding.

BACKGROUND ART

Recently, there is an increasing demand for a personalized medical industry to diagnose diseases early and increase survival rate through appropriate treatment. In particular, there is an increasing need for molecular diagnostic techniques capable of accurately measuring and analyzing the diseases in the molecular level, such as a DeoxyriboNucleic Acid (DNA) or a RiboNucleic Acid (RNA).

As a molecular diagnostic technology, there are a PCR (Polymerase Chain Reaction) diagnostic method and a Raman spectroscopic method. The PCR diagnostic method is a method that replicates and amplifies a desired part of a nucleic acid through a polymerase chain reaction, and measures a signal emitted from a fluorescence label attached to the amplified nucleic acid. The Raman spectroscopic method is a method of measuring and analyzing scattered light that generated from vibrations of nucleic acid molecules in a sample are excited by light.

DISCLOSURE

Technical Problem

The problem to be solved by the inventive concept is to provide a spectroscopic apparatus and a spectroscopic method that analyze biomolecules using a time resolved coding.

Technical Solution

The spectroscopic apparatus according to an embodiment of the inventive concept includes a laser irradiation device that receives an orthogonal code including a series of bits each having a first value or a second value, generates a control signal having a pulse that has a width shorter than a width of a bit section in the bit section corresponding to a bit having the first value among the series of bits, generates a pulsed laser beam having a pulse width shorter than the bit section using the pulse included in the control signal as a trigger, and irradiates an incident beam including the generated pulsed laser beam to a sample, and a detector that receives a detection signal generated from the sample to which the incident beam is irradiated and the orthogonal code, generates an orthogonal code signal of the same waveform as that of the incident beam, based on the orthogonal code, and demodulates a Raman signal, based on a correlation between the generated orthogonal code signal and the Raman signal included in the detection signal.

In an exemplary embodiment, the control signal has a first voltage or a second voltage greater than the first voltage, has the first voltage after having the second voltage in the bit section corresponding to the bit having the first value among the series of bits, and maintains the first voltage in another bit section corresponding to the bit having the second value among the series of bits.

In an exemplary embodiment, the laser irradiation device is further configured to generate the pulsed laser beam using a rising edge of the pulse included in the control signal as the trigger.

In an exemplary embodiment, the laser irradiation device is further configured to generate the pulsed laser beam using a falling edge of the pulse included in the control signal as the trigger.

In an exemplary embodiment, the laser irradiation device includes a main oscillator that receives the orthogonal code, and outputs a time resolved beam including the pulsed laser beam, and a power amplifier that receives the time resolved beam and amplifies the time resolved beam to irradiate the incident beam to the sample.

In an exemplary embodiment, the main oscillator includes a control signal generator that receives the orthogonal code and outputs the control signal, based on the received orthogonal code, a controller that receives the control signal and outputs a trigger signal for generating the pulsed laser beam, based on the control signal, and a light source that receives the trigger signal, includes time resolved width information for determining the pulse width of the pulsed laser beam, and outputs the time resolved beam, based on the received trigger signal and the time resolved width information.

In an exemplary embodiment, the power amplifier includes an isolator that receives the time resolved beam and blocks light reflected back to the light source.

In an exemplary embodiment, the power amplifier includes a first pump laser that outputs a first pump laser beam for optically pumping a gain medium, and a coupler that couples the time resolved beam and the first pump laser beam.

In an exemplary embodiment, the power amplifier further includes a second pump laser that outputs a second pump laser beam for optically pumping the gain medium, and the coupler is further configured to couple the time resolved beam, the first pump laser beam, and the second pump laser beam.

In an exemplary embodiment, the power amplifier includes a filter that passes a laser beam corresponding to a wavelength of the time resolved beam and blocks noise.

In an exemplary embodiment, the power amplifier includes a first amplification stage that receives the time resolved beam, and amplifies the received time resolved beam to output a first amplified time resolved beam, a second amplification stage that receives the first amplified time resolved beam, and outputs a second amplified time resolved beam in which the first amplified time resolved beam is further amplified, and a third amplification stage that receives the second amplified time resolved beam, and irradiates the incident beam in which the second amplified time resolved beam is further amplified to the sample.

The spectroscopic method according to an embodiment of the inventive concept includes generating an orthogonal code including a series of bits each having a first value or a second value, generating a control signal having a pulse that has a width shorter than a width of a bit section in the bit section corresponding to a bit having the first value among the series of bits, generating a pulsed laser beam having a pulse width shorter than the bit section using the pulse included in the control signal as a trigger, and irradiating an incident beam including the generated pulsed laser beam to a sample, receiving a detection signal output from the sample to which the incident beam is irradiated, generating an orthogonal code signal of the same waveform as that of the incident beam, based on the orthogonal code, and demodulating a Raman signal by calculating an autocorrelation coefficient, based on a correlation between the orthogonal code signal and the Raman signal included in the detection signal.

In an exemplary embodiment, the detection signal includes a Raman signal having a first intensity and being received at a first time, and a noise signal having a second intensity greater than the first intensity and being received at a second time later than the first time.

In an exemplary embodiment, the demodulating of the Raman signal further includes removing the noise signal, based on a correlation between the orthogonal code signal and the noise signal, and an intensity of the demodulated Raman signal is greater than an intensity of the removed noise signal.

In an exemplary embodiment, the detection signal includes the Raman signal having a first lifetime and a noise signal having a second lifetime longer than the first lifetime, and the pulse width of the pulsed laser beam is longer than the first lifetime and shorter than the second lifetime.

Advantageous Effects

According to an embodiment of the inventive concept, a spectroscopic apparatus and a spectroscopic method in which a signal-to-noise ratio of a biomolecules is improved by removing noise signals are provided.

In addition, a spectroscopic apparatus and a spectroscopic method are provided that reduce a measurement time required for molecular diagnosis and improve an accuracy, a resolution, and a definition of the molecular diagnosis.

BEST MODE

Figure 15:
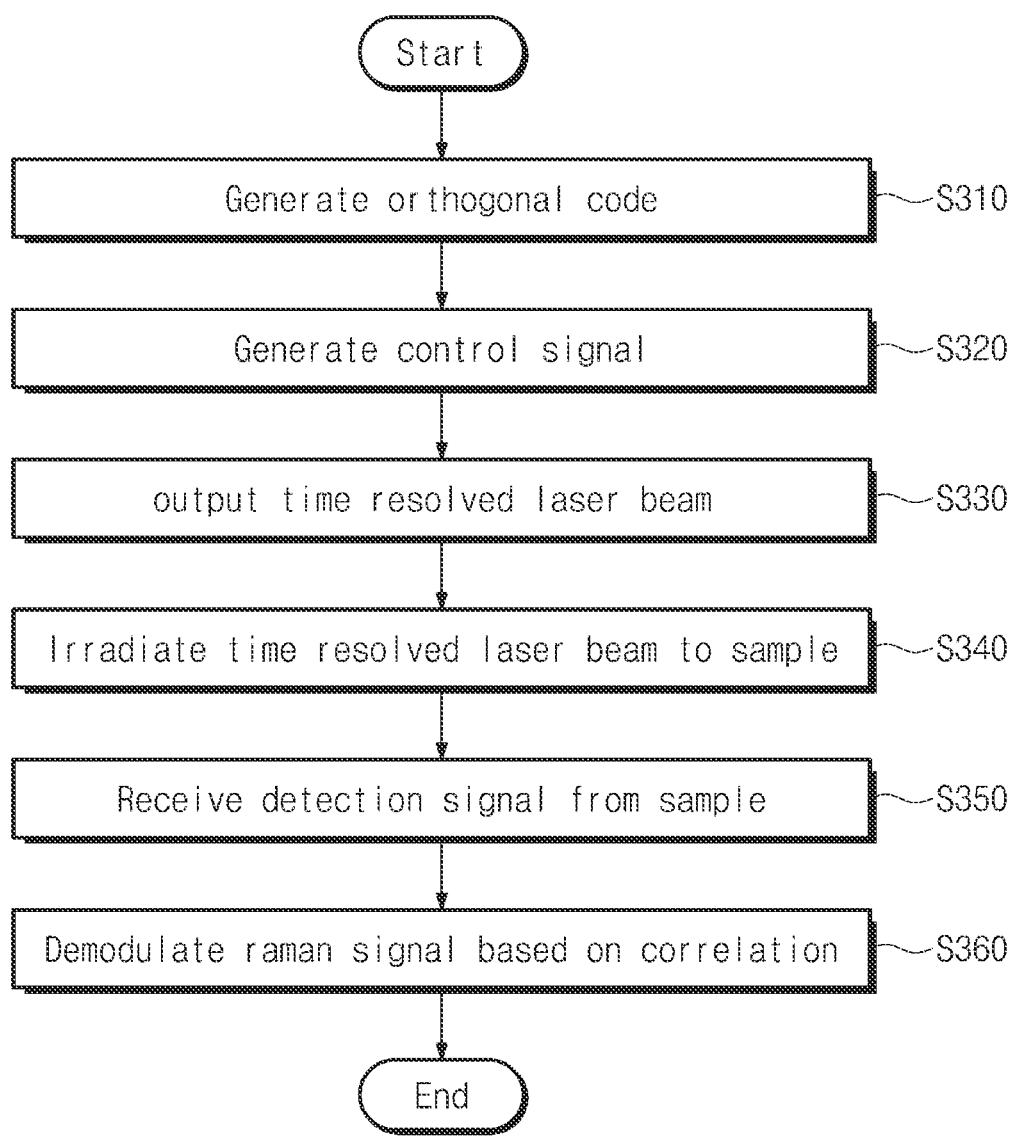
FIG. 15 is a flowchart illustrating a spectroscopic method for restoring a Raman signal according to an embodiment of the inventive concept.

FIG. 15 is a diagram representing the best mode for carrying out the inventive concept.

MODE FOR INVENTION

Hereinafter, embodiments of the inventive concept will be described clearly and in detail such that those skilled in the art may easily carry out the inventive concept.

Figure 1:
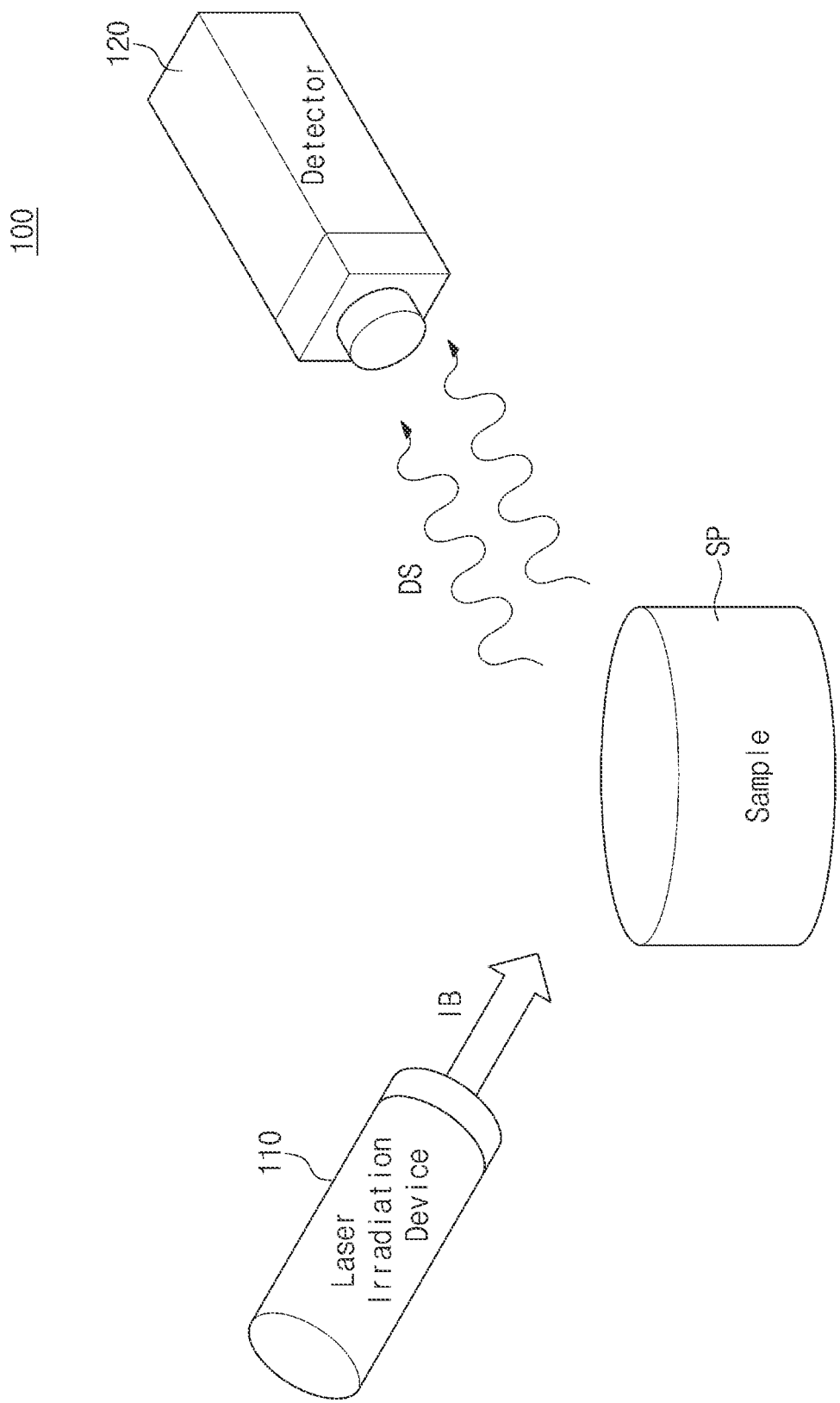
FIG. 1 is a diagram illustrating a spectroscopic apparatus according to an embodiment of the inventive concept.

FIG. 1 is a diagram illustrating a spectroscopic apparatus according to an embodiment of the inventive concept. Referring to FIG. 1, a spectroscopic apparatus 100 may include a laser irradiation device 110 and a detector 120. The spectroscopic apparatus 100 may be an apparatus that analyzes a sample SP. In this case, the sample SP may be bio sample molecules to be analyzed. For example, the sample SP may be feces including nucleic acids such as a DNA and an RNA.

The laser irradiation device 110 may irradiate an incident beam IB to the sample SP. The incident beam IB may be a laser beam generated by the laser irradiation device 110. A detection signal DS may be output from the sample SP to which the incident beam IB is irradiated. The detection signal DS may be a signal including molecular information of the sample SP. For example, the detection signal DS may be light emitted or scattered from the sample SP to which the incident beam IB is irradiated.

The detector 120 may receive the detection signal DS generated from the sample SP. The detector 120 may analyze the sample SP, based on the received detection signal DS. For example, the detector 120 may detect a signal including information of a virus causing a disease, which is contained in a fecal sample.

As described above, according to an embodiment of the inventive concept, by irradiating the incident beam to the sample SP, and by receiving and analyzing the detection signal DS generated from the sample SP, the spectroscopic apparatus 100 that analyzes the sample SP may be provided.

Figure 2:
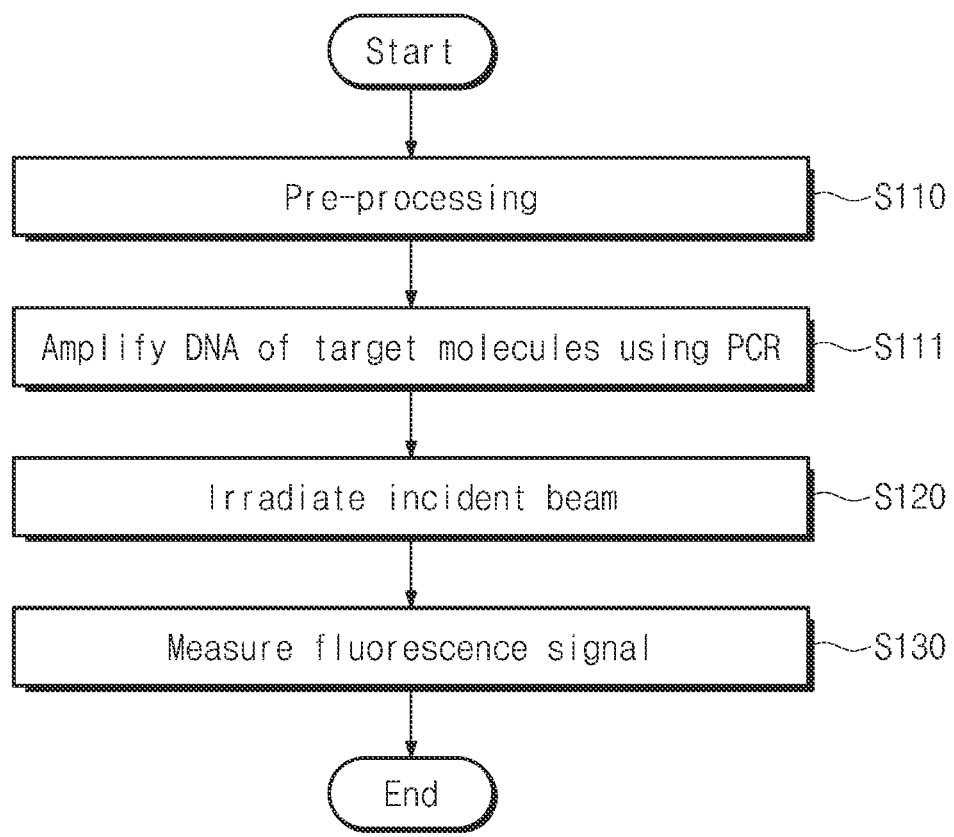
FIG. 2 is a flowchart illustrating a PCR molecular diagnostic method according to an embodiment of the inventive concept.

FIG. 2 is a flowchart illustrating a PCR molecular diagnostic method according to an embodiment of the inventive concept. For convenience of explanation, the PCR molecular diagnostic method according to the flow chart of FIG. 2 will be described with reference to the spectroscopic apparatus 100 of FIG. 1. Referring to FIGS. 1 and 2, a PCR molecular diagnostic method using a polymerase chain reaction is illustrated by way of example.

In step S110, a pre-processing with respect to the sample SP may be performed. For example, step S110 may be a step that performs a centrifuge, a DNA binding, a washing, an elution, and a purified plasmid DNA with respect to the sample SP.

In step S111, the spectroscopic apparatus may amplify DNA of target molecules using PCR. For example, the PCR amplification may be performed on the sample SP that is pre-processed. The PCR amplification may be a process of replicating and amplifying a desired part of a nucleic acid, based on the polymerase chain reaction. For example, step S111 may be a step of performing a DNA denaturation, a primer annealing, and a DNA extension. In an exemplary embodiment, after performing step S111, a step of attaching a fluorescence label to the sample SP on which the PCR amplification is performed may be further performed.

In step S120, the laser irradiation device 110 may irradiate the incident beam IB to the sample SP on which the PCR amplification is performed. The detection signal DS may be generated from the sample SP to which the incident beam IB is irradiated. In this case, the detection signal DS may include a fluorescence signal emitted from the fluorescence label attached to the sample SP.

In step S130, the detector 120 may measure the fluorescence signal emitted from the sample SP. The detector 120 may analyze the sample SP, based on the measured fluorescence signal. In an exemplary embodiment, by repeatedly performing the pre-processing step S110, the fluorescence signal with reduced noise and increased intensity may be measured.

Figure 3:
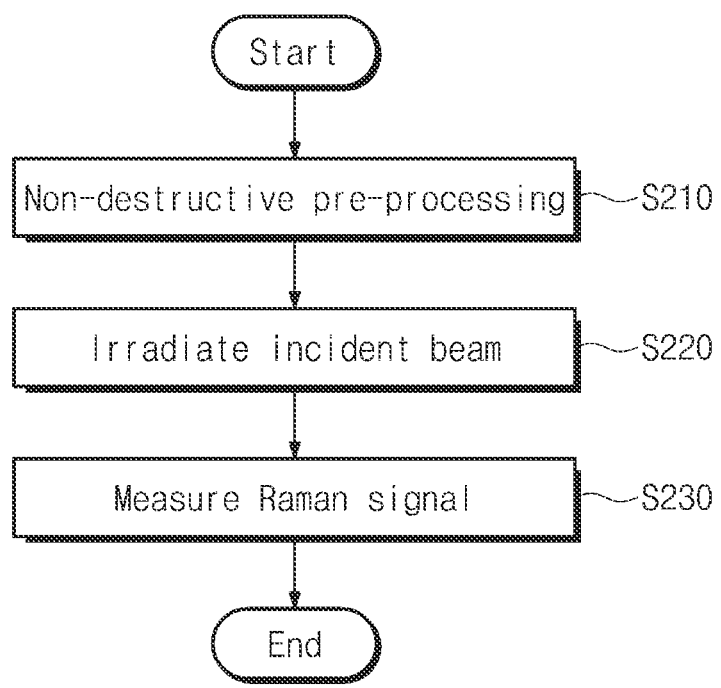
FIG. 3 is a flowchart illustrating a Raman spectroscopic method according to an embodiment of the inventive concept.

FIG. 3 is a flowchart illustrating a Raman spectroscopic method according to an embodiment of the inventive concept. For convenience of explanation, the Raman spectroscopic method according to the flowchart of FIG. 3 will be described with reference to the spectroscopic apparatus 100 of FIG. 1. Referring to FIGS. 1 and 3, the Raman spectroscopic method is illustrated by way of example.

In step S210, a non-destructive pre-processing may be performed on the sample SP. In contrast to the pre-processing step S110 and the PCR amplification step S111 of FIG. 2, in step S210, a process that destroys cell walls and amplifies the nucleic acid may be omitted. In an exemplary embodiment, step S210 may be omitted. Accordingly, a spectroscopic method in which a time required for diagnosis is shortened may be provided.

In step S220, the laser irradiation device 110 may irradiate the incident beam IB to the sample SP. The detection signal DS may be generated from the sample SP to which the incident beam IB is irradiated. In this case, the detection signal DS may include a Raman signal and a noise signal. For example, the noise signal may include a fluorescence noise signal.

In step S230, the detector 120 may measure the Raman signal that is scattered from the sample SP. The detector 120 may analyze the sample SP, based on the measured Raman signal. In this case, the Raman signal may be a signal having a narrower bandwidth, shorter lifetime, and weak intensity than the fluorescence signal measured in step S130 of FIG. 2. In an exemplary embodiment, when the detector 120 analyzes the sample SP with a signal having the narrow bandwidth, a measurement resolution on the sample SP may be high.

As described above, according to an embodiment of the inventive concept, the Raman spectroscopic method with improved measurement resolution may be provided by analyzing the sample, based on a Raman signal having a narrower bandwidth than the fluorescence signal. In addition, by omitting the process (e.g., S111 in FIG. 2) of amplifying the nucleic acid, a Raman spectroscopic method in which the time required for diagnosis is shortened may be provided.

Figure 4A:
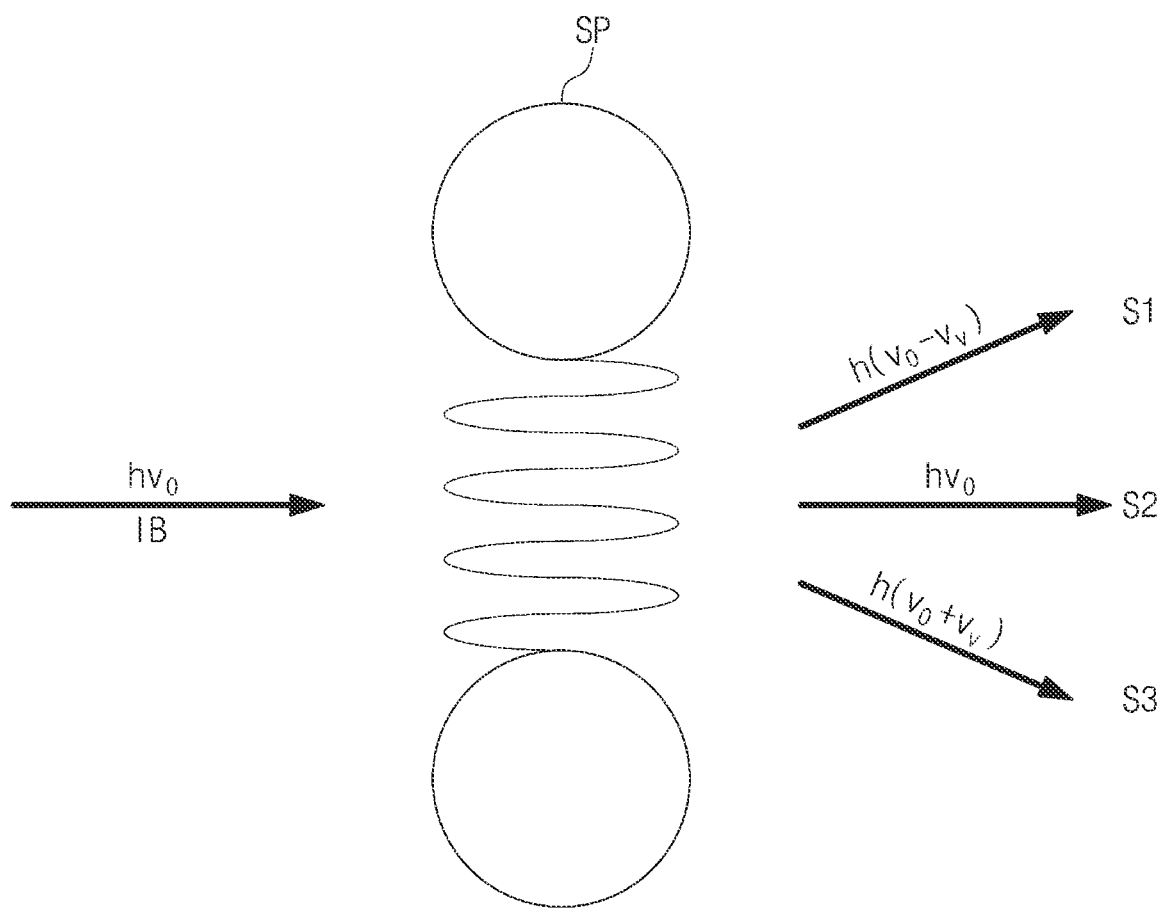
FIG. 4A is a diagram exemplarily describing a Raman scattered signal generated from a sample.

FIG. 4A is a diagram exemplarily describing a Raman scattering signal generated from a sample. Referring to FIG. 4A, scattering signals S1 to S3 generated from the sample SP to which the incident beam IB is irradiated are illustrated by way of example. The incident beam IB may be a laser beam having an incident frequency $v_0$. The energy of the incident beam IB may be '$hv_0$'. In this case, 'h' may be a Boltzmann constant. A vibration energy of the sample SP to which the incident beam IB is irradiated may increase, maintain, or decrease.

In an exemplary embodiment, the first scattering signal S1 may be generated from the sample SP to which the incident beam IB is irradiated. The first scattering signal S1 may be a stokes scattering signal. In this case, energy of the sample SP after the incident beam IB is irradiated may be greater than energy of the sample SP before the incident beam IB is irradiated. Energy $h(v_0-v_v)$ of the first scattering signal S1 may be less than energy $hv_0$ of the incident beam IB.

In an exemplary embodiment, the second scattering signal S2 may be generated from the sample SP to which the incident beam IB is irradiated. The second scattering signal S2 may be a Rayleigh scattering signal. In this case, the energy of the sample SP after the incident beam IB is irradiated may be the same as the energy of the sample SP before the incident beam IB is irradiated. The energy $hv_0$ of the second scattering signal S2 may be the same as the energy $hv_0$ of the incident beam IB.

In an exemplary embodiment, the third scattering signal S3 may be generated from the sample SP to which the incident beam IB is irradiated. The third scattering signal S3 may be an anti-stokes scattering signal. In this case, the energy of the sample SP after the incident beam IB is irradiated may be less than the energy of the sample SP (e.g., sample molecules) before the incident beam IB is irradiated. Energy $h(v_0+v_v)$ of the third scattering signal S3 may be greater than the energy $hv_0$ of the incident beam IB.

As described above, according to an embodiment of the inventive concept, the Raman scattering signal generated from the sample molecules to which the incident beam IB is irradiated may include the first scattering signal S1, which is the Stokes scattering signal, the second scattering signal S2, which is the Rayleigh scattering signal, and the third scattering signal S3, which is the anti-stokes scattering signal.

Figure 4B:
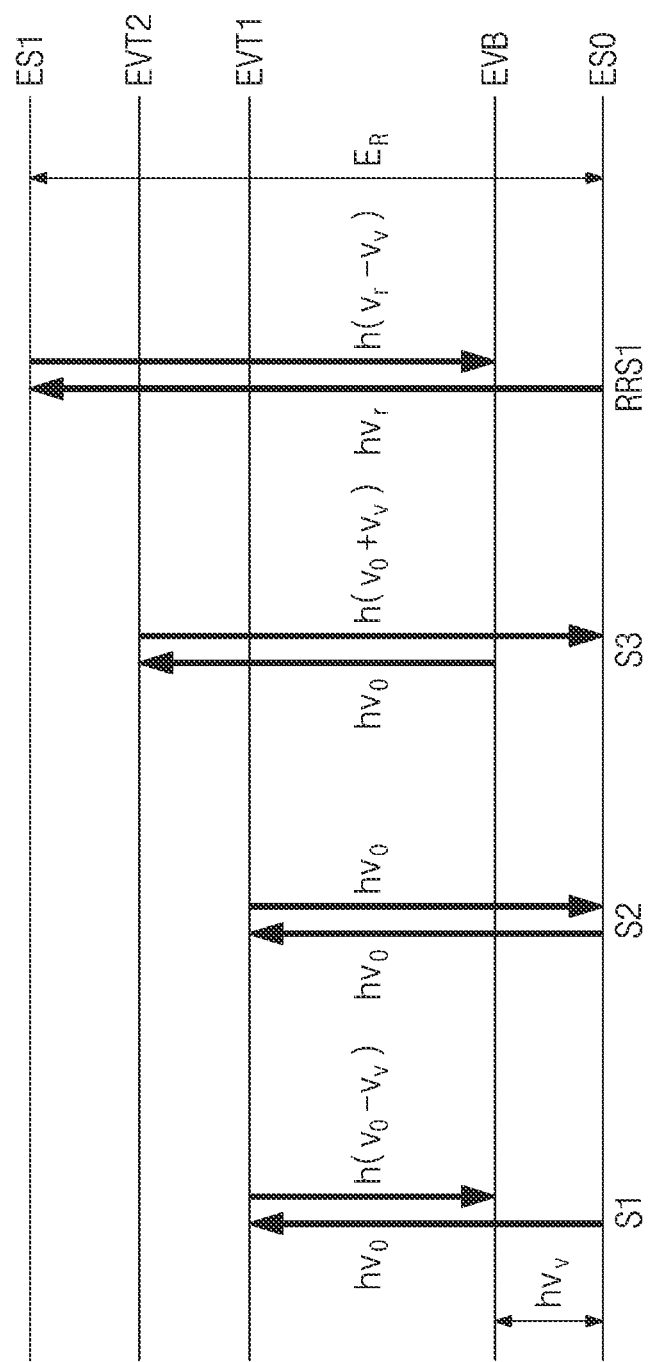
FIG. 4B is a graph illustrating an energy level diagram of sample molecules depending on generation of a Raman scattering signal in FIG. 4A.

FIG. 4B is a graph illustrating a process of generating a Raman scattering signal depending on an vibration energy of sample molecules due to an incident beam in FIG. 4A. Referring to FIG. 4B, a process of generating each of the scattering signals S1 to S3 depending on the vibration energy of the sample molecules is illustrated by way of example.

In addition, a process of generating a first resonance Raman scattering signal RRS1 depending on the energy change of the sample molecules due to the incident beam is illustrated. The first resonance Raman scattering signal RRS1 may be the Stokes scattering signal generated based on a resonance Raman effect. The resonance Raman effect may be an effect of remarkably increasing the intensity of the Raman scattering signal when the incident beam having resonance energy $E_R$ is irradiated. The resonance energy $E_R$ may mean an interval between energies that electrons of a specific material may have. For example, the resonance energy $E_R$ may be a band gap of a sample.

Referring to a generation process of the first scattering signal S1 depending on the vibration energy of the sample due to the incident beam, the sample before the incident beam is irradiated may have energy of a ground state level ES0. The spectroscopic apparatus may irradiate the incident beam having the energy of '$hv_0$' to the sample. The sample excited by the incident beam may have the energy of a first virtual state level EVT1. The first scattering signal S1 having the energy of '$h(v_0-v_v)$' may be generated in the excited sample. The sample in which the first scattering signal S1 is generated may have the energy of a vibration state level EVB. That is, the energy of the sample to which the incident beam is irradiated may increase by 'hv$_v$'.

Referring to a generation process of the second scattering signal S2 depending on the vibration energy of the sample due to the incident beam, the sample before the incident beam is irradiated may have the energy of the ground state level ES0. The spectroscopic apparatus may irradiate the incident beam having the energy of 'hv$_0$' to the sample. The sample excited by the incident beam may have the energy of the first virtual state level EVT1. The second scattering signal S2 having the energy of 'hv$_0$' may be generated from the excited sample. The sample in which the second scattering signal S2 is generated may have the energy of the ground state level ES0. That is, the energy of the sample after the incident beam is irradiated may be the same as the energy of the sample before the incident beam is irradiated.

In an exemplary embodiment, the second scattering signal S2 may be a signal inadequate to reflect characteristics of the sample. In more detail, the second scattering signal S2 may have the same energy as the incident beam. The second scattering signal S2 may not reflect the energy change due to molecular vibration of the sample. That is, the second scattering signal S2 may be a signal that does not reflect the characteristics of the sample.

Referring to a generation process of the third scattering signal S3 depending on the vibration energy of the sample due to the incident beam, the sample before the incident beam is irradiated may have the energy of the vibration state level EVB. The spectroscopic apparatus may irradiate the incident beam having the energy of 'hv$_0$' to the sample. The sample excited by the incident beam may have the energy of a second virtual state level EVT2. The third scattering signal S3 having the energy of 'h(v$_0$+v$_v$)' may be generated from the excited sample. The sample in which the third scattering signal S3 is generated may have the energy of the ground state level ES0. That is, the energy of the sample to which the incident beam is irradiated may decrease by 'hv$_v$'.

Referring to a generation process of the first resonance Raman scattering signal RRS1 depending on the vibration energy of the sample due to the incident beam, the sample before the incident beam is irradiated may have the energy of the ground state level ES0. The spectroscopic apparatus may irradiate the incident beam having the energy of 'hv$_r$' equal to the resonance energy $E_R$ to the sample. The sample excited by the incident beam may have the energy of the first energy state level ES1. The first resonance Raman scattering signal RRS1 having the energy of 'h(v$_r$-v$_v$)' may be generated from the excited sample. The sample in which the first resonance Raman scattering signal RRS1 is generated may have the energy of the vibration state level EVB. That is, the energy of the sample to which the incident beam is irradiated may increase by 'hv$_v$'.

In an exemplary embodiment, a spectroscopic apparatus for measuring a resonance Raman scattering signal having a stronger intensity than a typical Raman scattering signal may be provided by irradiating an incident beam having the resonance energy $E_R$ to a sample. For example, the energy h(v$_r$-v$_v$) of the first resonance Raman scattering signal RRS1 obtained based on the incident beam having the resonance energy $E_R$ may be greater than the energy h(v$_0$-v$_v$) of the first scattering signal S1 obtained based on the incident beam having energy of 'hv$_0$' that is not related to the resonance energy $E_R$.

As described above, according to an embodiment of the inventive concept, a spectroscopic apparatus may be provided that reflects the characteristics of the sample and analyzes the characteristics of the sample based on the third scattering signal S3 or the first scattering signal S1. In addition, by irradiating the incident beam having the resonance energy $E_R$ to the sample, a spectroscopic apparatus for measuring the first resonance Raman scattering signal RRS1 having a stronger intensity than the first scattering signal S1 may be provided.

Figure 5:
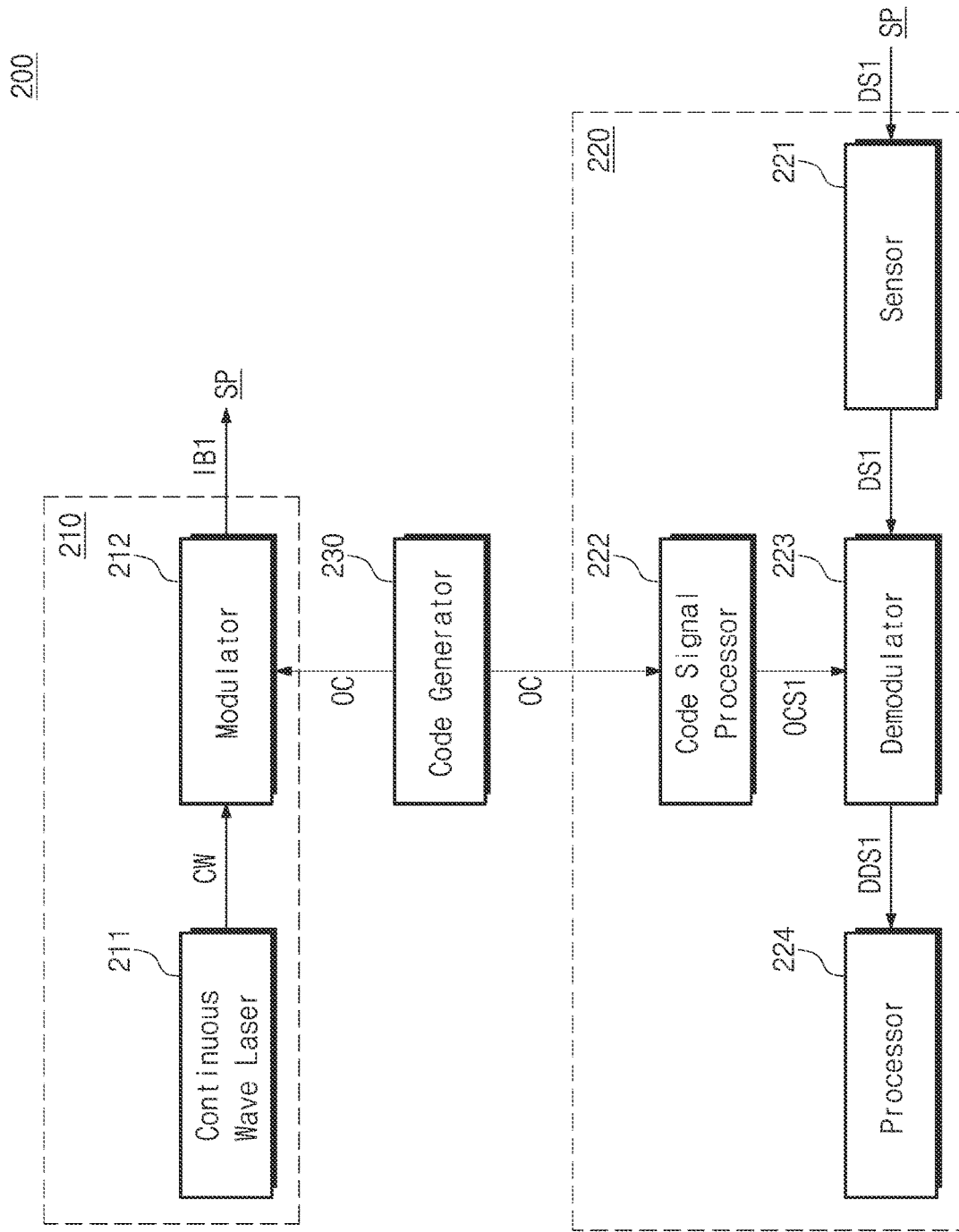
FIG. 5 is a block diagram illustrating a Raman spectroscopic apparatus using a spread spectrum code according to an embodiment of the inventive concept.

FIG. 5 is a block diagram illustrating a spectroscopic apparatus according to an embodiment of the inventive concept. Referring to FIG. 5, a spectroscopic apparatus 200 may include a laser irradiation device 210, a detector 220, and a code generator 230. The spectroscopic apparatus 200 may be a spectrometer that analyzes the Raman signal included in a first detection signal DS1 that is generated from the sample SP.

The code generator 230 may generate an orthogonal code OC. The orthogonal code OC may be a code having mathematically orthogonality with other codes. The orthogonal code OC may include a plurality of bits corresponding to a series of numbers. The code generator 230 may output the generated orthogonal code OC to the laser irradiation device 210 and the detector 220.

In an exemplary embodiment, the laser irradiation device 210 and the detector 220 may be synchronized based on the orthogonal code OC output from the code generator 230. In more detail, the orthogonal code OC may allow the laser irradiation device 210 to modulate a continuous wave signal CW. The orthogonal code OC may allow the detector 220 to demodulate the first detection signal DS1.

The laser irradiation device 210 may include a continuous wave laser 211 and a modulator 212. The continuous wave laser 211 may generate the continuous wave signal CW. The continuous wave signal CW may be a laser beam having a uniform intensity. The modulator 212 may receive the continuous wave signal CW from the continuous wave laser 211. The modulator 212 may receive the orthogonal code OC from the code generator 230. The modulator 212 may irradiate a first incident beam IB1 obtained by modulating the continuous wave signal CW into the orthogonal code OC pattern to the sample SP.

The detector 220 may include a sensor 221, a code signal processor 222, a demodulator 223, and a processor 224. The sensor 221 may receive the first detection signal DS1 from the sample SP. The sensor 221 may sense the received first detection signal DS1. The sensor 221 may output the sensed first detection signal DS1 to the demodulator 223. That is, the sensor 221 may be a module that senses the first detection signal DS1 output from the sample SP, and converts the detected first detection signal DS1 into an electrical signal that may be processed by the demodulator 223 and then transfers the electrical signal.

The code signal processor 222 may receive the orthogonal code OC from the code generator 230. The code signal processor 222 may output a first orthogonal code signal OCS1, based on the received orthogonal code OC. The first orthogonal code signal OCS1 may be an electrical signal having the same waveform as the first incident beam IB1. For example, a time of the first orthogonal code signal OCS1 corresponding to a specific bit of the orthogonal code OC may be the same as a time of the first incident beam IB1.

The demodulator 223 may receive the first detection signal DS1 from the sensor 221. The demodulator 223 may receive the first orthogonal code signal OCS1 from the code signal processor 222. The demodulator 223 may output a first demodulated detection signal DDS1.

The first demodulated detection signal DDS1 may be a signal obtained by demodulating the first detection signal DS1 by calculating an autocorrelation coefficient, based on the correlation between the first detection signal DS1 and the first orthogonal code signal OCS1. That is, the demodulator 223 may be a module that restores the first detection signal DS1, based on the first orthogonal code signal OCS1.

The processor 224 may receive the first demodulated detection signal DDS1 from the demodulator 223. The processor 224 may analyze molecular information of the sample SP by a combination of Raman frequencies corresponding to a peak of the Raman signal that appears in the Raman spectrum, based on the Raman signal included in the first demodulated detection signal DDS1.

In an exemplary embodiment, due to a noise reduction effect by an delta function-like autocorrelation property of the orthogonal code, a signal-to-noise ratio of the first demodulated detection signal DDS1 obtained based on the orthogonal code OC may be greater than a signal-to-noise ratio of the detection signal that is not subjected to code modulation and demodulation and a signal-to-noise ratio of the detection signal that is demodulated based on an arbitrary code (e.g., a general code with poor autocorrelation property). The signal-to-noise ratio may mean that the intensity of the Raman signal is divided by an intensity of the noise signal. In this case, the arbitrary code may mean a code that does not have mathematically orthogonality with other codes.

As described above, according to an embodiment of the inventive concept, a spectroscopic apparatus may be provided that irradiates the first incident beam IB1 obtained by modulating the continuous wave signal CW, based on the orthogonal code OC to the sample SP, and demodulates the first detection signal DS1 output from the sample SP to analyze the sample SP.

Figure 6:
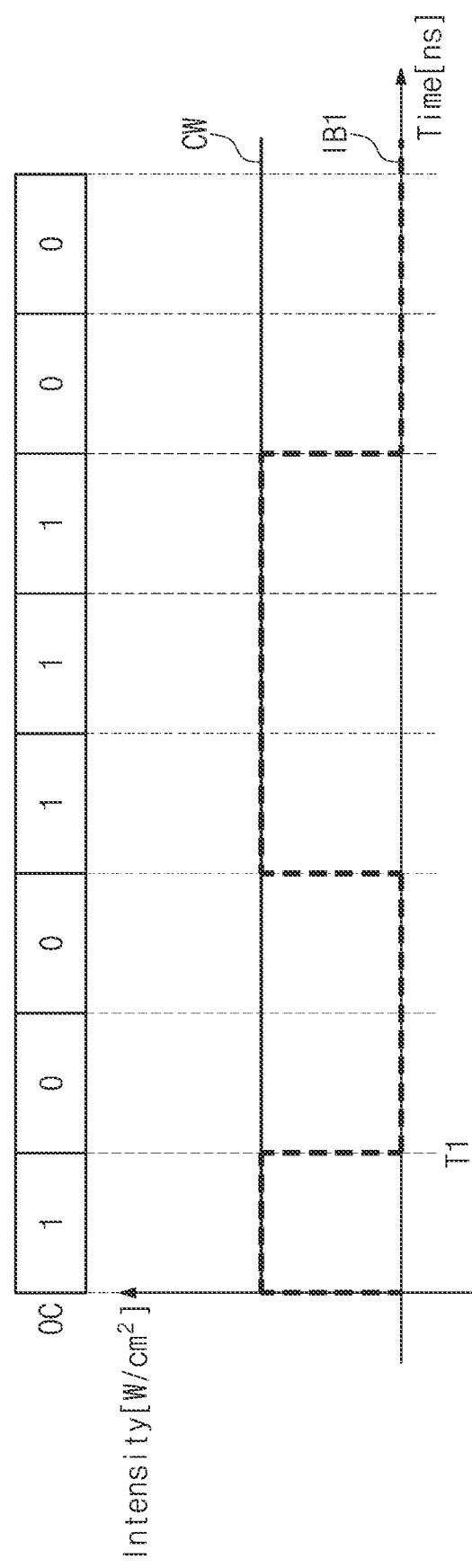
FIG. 6 is a graph illustrating signals generated by a laser irradiation device of FIG. 5.

FIG. 6 is a graph illustrating signals generated by a laser irradiation device of FIG. 5. Referring to FIGS. 5 and 6, a series of bits included in the orthogonal code OC, a waveform of the continuous wave signal CW, and a waveform of the first incident beam IB1 are illustrated by way of example. The modulator 212 may output the first incident beam IB1 obtained by modulating the continuous wave signal CW, based on the orthogonal code OC to the sample SP.

The orthogonal code (OC) may be a code including a series of bits. The series of bits may be a code having mathematically orthogonality with bits of other codes. Each bit may have a value of '1' or '0'. For example, a value of the series of bits included in the orthogonal code OC may be '10011100'.

In an exemplary embodiment, the first incident beam IB1 may be irradiated to the sample in a section corresponding to a bit having the value of '1' among bits included in the orthogonal code OC. The first incident beam IB1 may not be irradiated to the sample in a section corresponding to a bit having the value of '0' among bits included in the orthogonal code OC.

In an exemplary embodiment, the modulator 212 may modulate the continuous wave signal CW such that a length of the section corresponding to each of the bits included in the orthogonal code OC becomes a first time T1.

Figure 7:
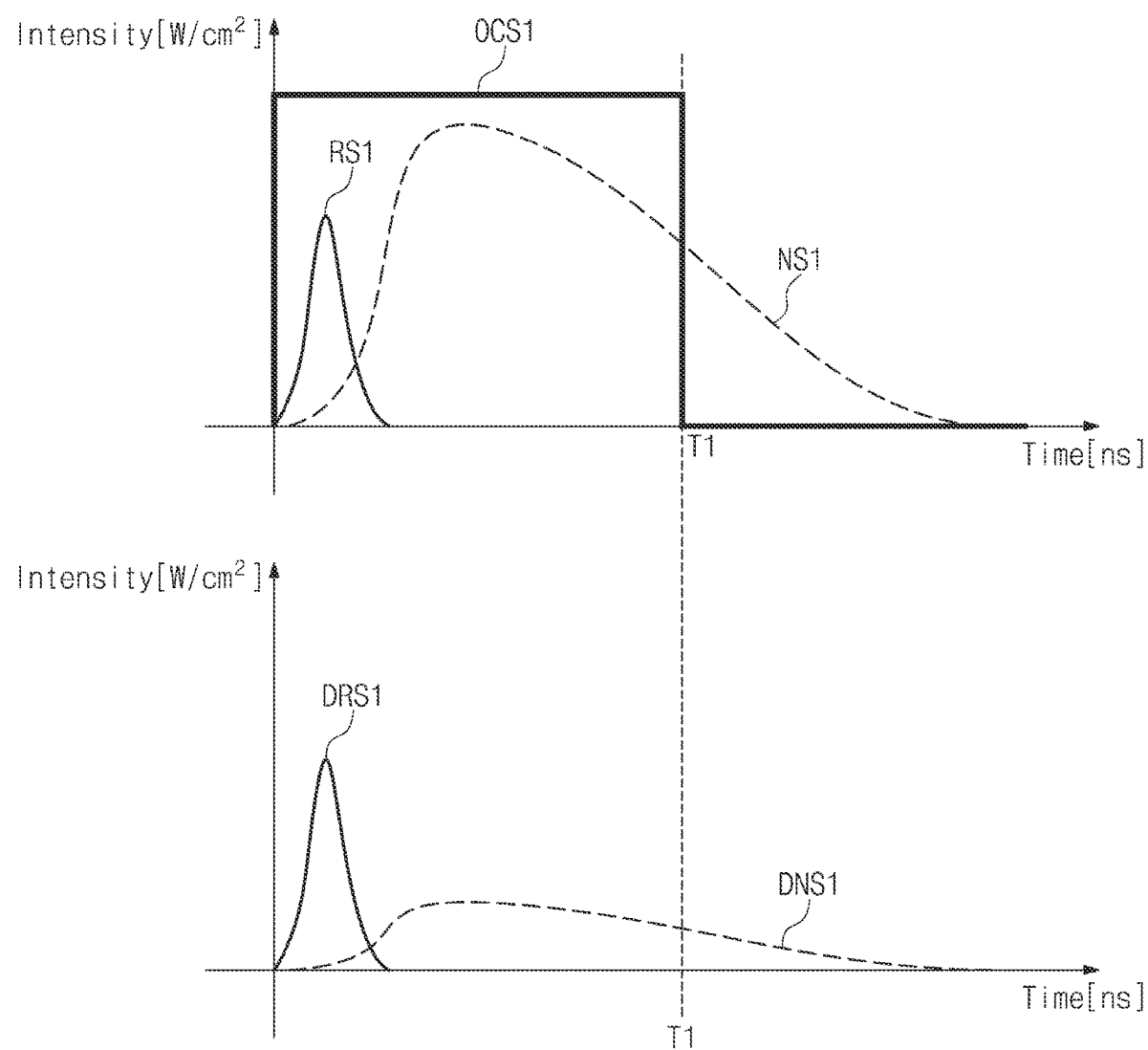
FIG. 7 is a graph illustrating signals processed by a detector of FIG. 5.

FIG. 7 is a graph illustrating signals processed by a detector of FIG. 5. Referring to FIGS. 5 and 7, a first Raman signal RS1 and a first noise signal NS1 that are included in the first detection signal DS1 are illustrated. In addition, a first demodulated Raman signal DRS1 and a first removed noise signal DNS1 that are included in the first demodulated detection signal DDS1 are illustrated.

In an exemplary embodiment, the demodulator 223 may receive the first detection signal DS1 including the first Raman signal RS1 and the first noise signal NS1. The demodulator 223 may receive the first orthogonal code signal OCS1 from the code signal processor 222. In this case, a waveform of the first orthogonal code signal OCS1 may be the same as the waveform of the first incident beam IB1 of FIG. 6. That is, the first orthogonal code signal OCS1 may be a signal synchronized with the first incident beam IB1.

The first Raman signal RS1 may have a lower intensity than the first noise signal NS1. The first Raman signal RS1 may have a shorter lifetime than the first noise signal NS1. The first Raman signal RS1 may be a signal that is measured in temporal priority over the first noise signal NS1. For example, the first noise signal NS1 may be the fluorescence noise signal.

In an exemplary embodiment, the demodulator 223 may obtain the first demodulated Raman signal DRS1 by restoring the first Raman signal RS1, based on the correlation between the first orthogonal code signal OCS1 and the first Raman signal RS1. The demodulator 223 may obtain the first removed noise signal DNS1 by canceling the first noise signal NS1 based on the correlation between the first orthogonal code signal OCS1 and the first noise signal NS1.

In this case, a signal-to-noise ratio of the first demodulated Raman signal DRS1 processed by the autocorrelation coefficient and the first removed noise signal DNS1 processed by a cross-correlation coefficient may be greater than a signal-to-noise ratio of the first Raman signal RS1 and the first noise signal NS1.

The processor 224 may analyze the molecular information of the sample SP, based on intensity, center frequency, bandwidth of the first demodulated Raman signal DRS1 included in the first demodulated detection signal DDS1. In this case, as the intensity of the first demodulated Raman signal DRS1 is greater than the intensity of the first removed noise signal DNS1, the processor 224 may obtain the molecular information having higher accuracy and resolution.

As described above, according to an embodiment of the inventive concept, by restoring the first Raman signal RS1 and removing the first noise signal NS1, based on the correlation with the first orthogonal code signal OCS1, the detector 220 including the demodulator 223 may be provided that improves the signal-to-noise ratio of the first demodulated Raman signal DRS1.

Figure 8:
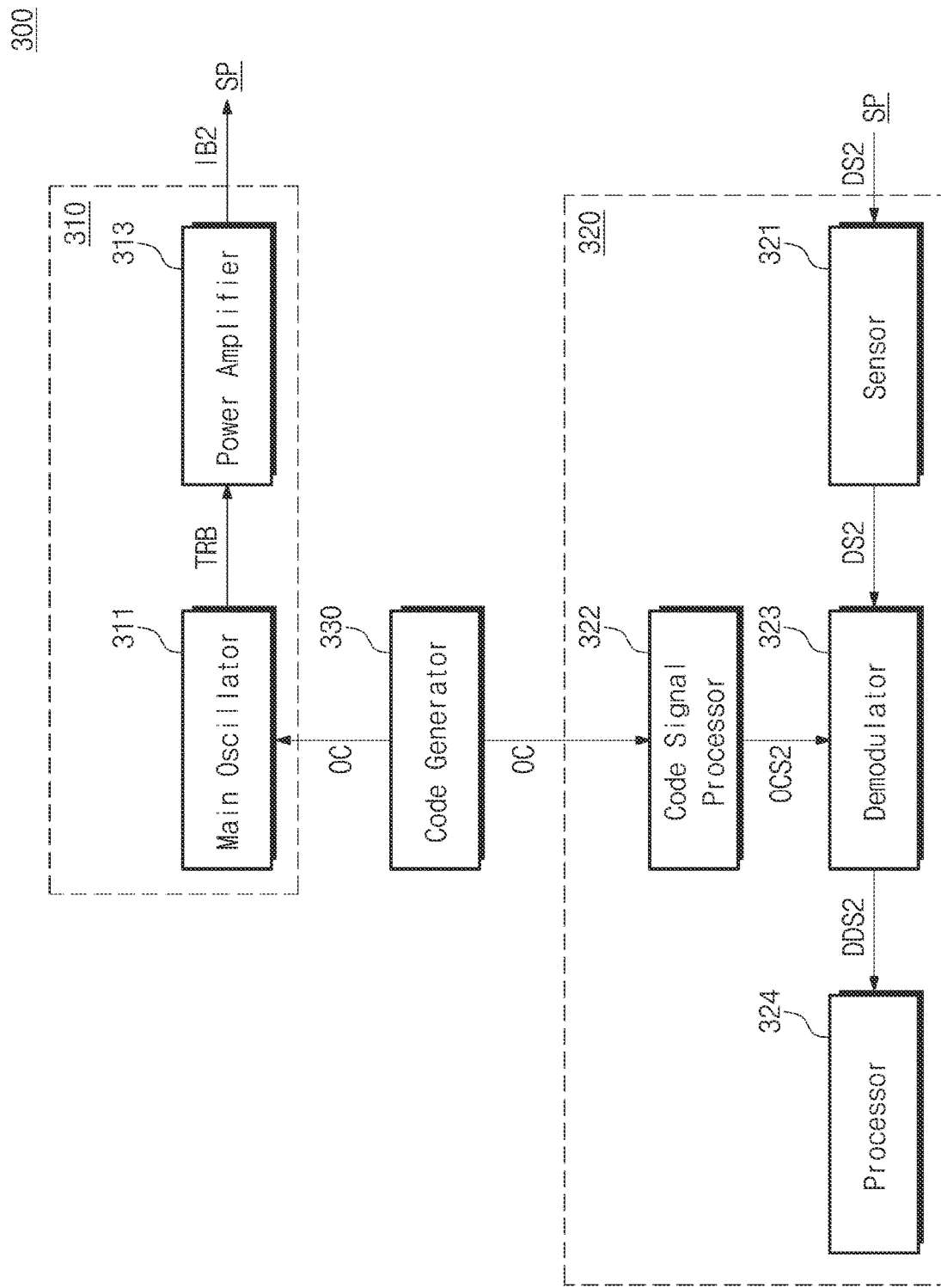
FIG. 8 is a block diagram exemplarily describing a Raman spectroscopic apparatus using a time resolved coding according to an embodiment of the inventive concept.

FIG. 8 is a block diagram exemplarily describing a spectroscopic apparatus according to an embodiment of the inventive concept. Referring to FIG. 8, a spectroscopic apparatus 300 may include a laser irradiation device 310, a detector 320, and a code generator 330. Since an operation of a sensor 321, a demodulator 323, a processor 324, and the code generator 330 is similar to the operation of the sensor 221, the demodulator 223, the processor 224, and the code generator 230 of FIG. 5, detailed descriptions thereof will be omitted.

The laser irradiation device 310 may include a main oscillator 311 and a power amplifier 313. The laser irradiation device 310 may be a laser device having a master oscillator power amplifier (MOPA) structure including a main oscillator that oscillates a pulse and a power amplifier that amplifies the pulse.

The main oscillator 311 may receive the orthogonal code OC from the code generator 330. The main oscillator 311 may output a time resolved beam TRB, based on the received orthogonal code OC. In this case, the time resolved beam TRB may be a laser beam that includes bit information of the orthogonal code OC and has a width corresponding to a bit narrower than that of the first incident beam IB1 of FIG. 5. That is, a second incident beam IB2 may have a higher modulation frequency than that of the first incident beam IB1 of FIG. 5.

The power amplifier 313 may receive the time resolved beam TRB from the main oscillator 311. The power amplifier 313 may irradiate the second incident beam IB2 obtained by amplifying the time resolved beam TRB to the sample SP. That is, the power amplifier 313 may be a module that amplifies the intensity of the time resolved beam TRB.

A code signal processor 322 may receive the orthogonal code OC from the code generator 330. The code signal processor 322 may output a second orthogonal code signal OCS2, based on the received orthogonal code OC. The second orthogonal code signal OCS2 may be an electrical signal having the same waveform as the second incident beam IB2. That is, the second orthogonal code signal OCS2 may be a signal having a higher modulation frequency than the first orthogonal code signal OCS1 of FIG. 5.

As described above, according to an embodiment of the inventive concept, the spectroscopic apparatus 300 may be provided that irradiates the second incident beam IB2 having a higher modulation frequency than the first incident beam IB1 of FIG. 5 to the sample SP by generating the time resolved beam TRB having a high modulation frequency using the main oscillator 311, and performs the demodulation with the second orthogonal code signal OCS2 having a higher modulation frequency than the first orthogonal code signal OCS1 of FIG. 5.

Figure 9:
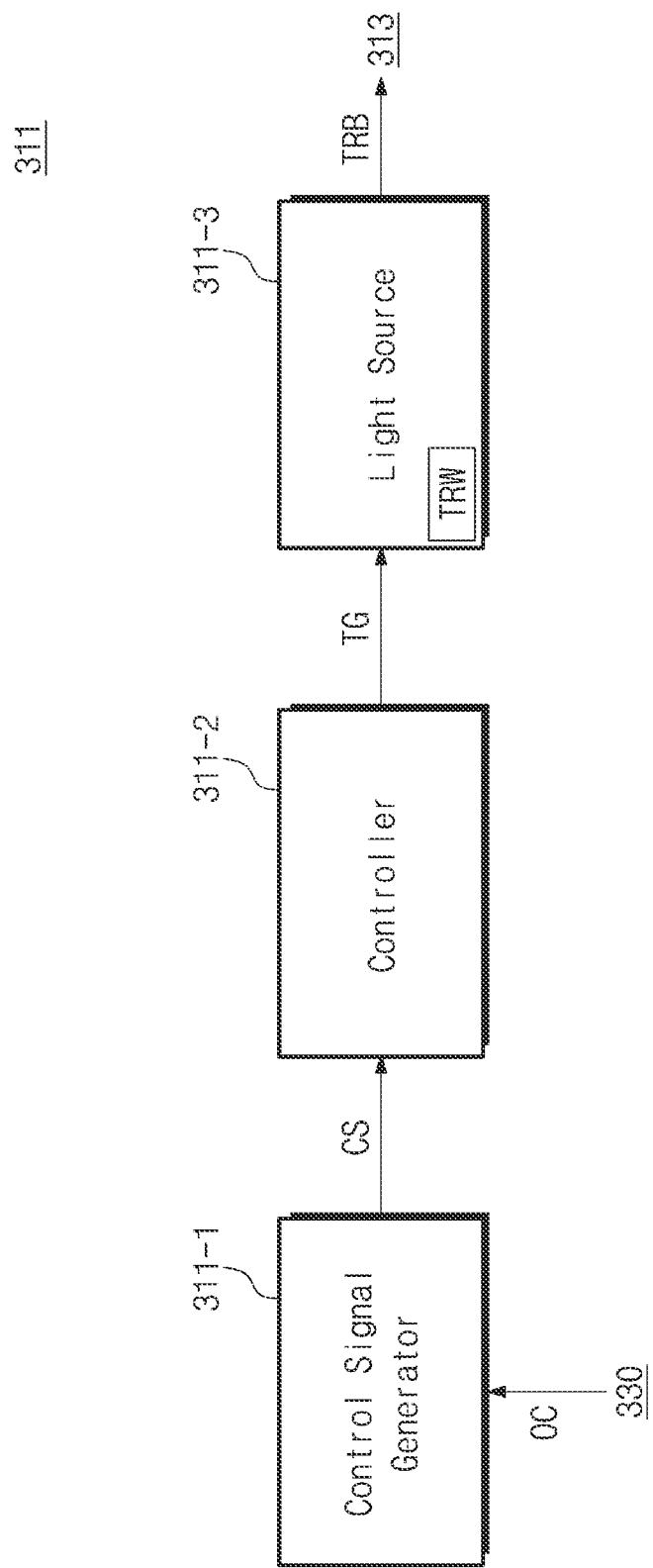
FIG. 9 is a block diagram exemplarily describing a main oscillator of FIG. 8.

FIG. 9 is a block diagram exemplarily describing a main oscillator of FIG. 8. Referring to FIG. 9, the main oscillator 311 may include a control signal generator 311-1, a controller 311-2, and a light source 311-3.

The control signal generator 311-1 may receive the orthogonal code OC from the code generator 330. The control signal generator 311-1 may output a control signal CS, based on the received orthogonal code OC. The control signal CS may be a pulse signal having an arbitrary duty ratio.

For example, in a section corresponding to a bit having the value of '1' among the bits included in the orthogonal code OC, the control signal CS may have a pulse. In a section corresponding to a bit having the value of '0' among the bits included in the orthogonal code OC, the control signal CS may maintain a unchanged value.

The controller 311-2 may receive the control signal CS from the control signal generator 311-1. The controller 311-2 may output a trigger signal TG, based on the received control signal CS. The trigger signal TG may be a signal that allows the light source 311-3 to output the pulsed laser beam in response to the pulse included in the control signal CS. That is, the trigger signal TG may be a signal that controls a generation time of the pulsed laser beam, based on a voltage fluctuation of the control signal CS. In this case, the pulsed laser beam may be a laser beam included in the time resolved beam TRB.

In an exemplary embodiment, the controller 311-2 may detect a rising edge of the control signal CS. The controller 311-2 may allow the light source 311-3 to output the pulsed laser beam when the rising edge occurs.

In an exemplary embodiment, the controller 311-2 may detect a falling edge of the control signal CS. The controller 311-2 may allow the light source 311-3 to output the pulsed laser beam when the falling edge occurs.

The light source 311-3 may receive the trigger signal TG from the controller 311-2. The light source 311-3 may have time resolved width information TRW. The light source 311-3 may output the time resolved beam TRB including the pulsed laser beam that is generated based on the trigger signal TG and the time resolved width information TRW to the power amplifier 313.

In this case, the time resolved width information TRW may be information indicating a pulse width of the pulsed laser beam included in the time resolved beam TRB. The time resolved beam TRB may include pulsed laser beams generated depending on the trigger signal TG. A pulse width of each of the generated pulsed laser beams may be determined based on the time resolved width information TRW.

In an exemplary embodiment, the light source 311-3 may be a module that outputs the pulsed laser beam having a short pulse width. For example, the light source 311-3 may include a distributed feedback (DFB) laser diode.

In an exemplary embodiment, by controlling a timing at which the light source 311-3 outputs a pulsed laser beam, based on the orthogonal code OC, the light source 311-3 that outputs the same pulsed laser beam as modulated at high frequency without a separate modulator may be provided. In this case, the time resolved beam TRB output from the light source 311-3 may include bit information of the orthogonal code OC.

In an exemplary embodiment, the pulsed laser beam included in the time resolved beam TRB output from the light source 311-3 may have a narrow pulse width and a strong intensity. For example, the pulse width of the pulsed laser beam may be 1 [ns]. A peak power output of the main oscillator 311 that outputs the time resolved beam TRB may be 1 [W].

Figure 10:
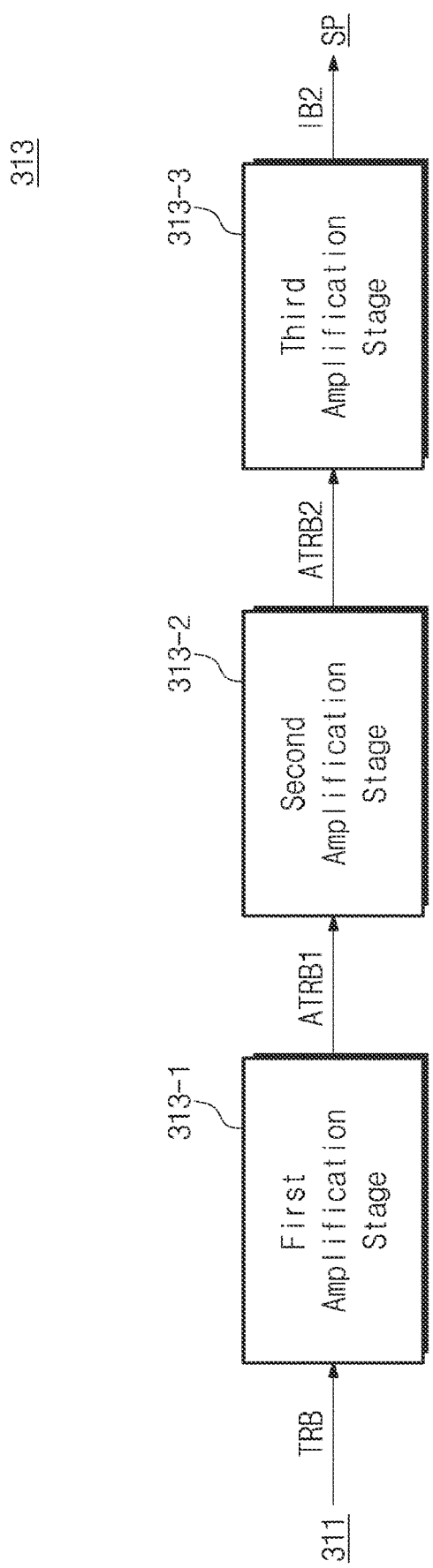
FIG. 10 is a block diagram exemplarily describing a power amplifier of FIG. 8.

FIG. 10 is a block diagram exemplarily describing a power amplifier of FIG. 8. Referring to FIG. 10, the power amplifier 313 may include a first amplification stage 313-1, a second amplification stage 313-2, and a third amplification stage 313-3. That is, the power amplifier 313 may be an amplifier including a plurality of amplifier stages. The power amplifier 313 in FIG. 10 is illustrated to include '3' amplification stages, but the scope of the inventive concept is not limited thereto, and the number of amplification stages included in the power amplifier 313 may increase or decrease.

The first amplification stage 313-1 may receive the time resolved beam TRB from the main oscillator 311. The first amplification stage 313-1 may output a first amplified time resolved beam ATRB1 obtained by amplifying the received time resolved beam TRB. For example, the output power of the first amplification stage 313-1 may be about 0.1 to 1 [mW].

The first amplification stage 313-1 may have a core pumping structure. In an exemplary embodiment, the first amplification stage 313-1 may have a cladding pumping structure instead of the core pumping structure.

The second amplification stage 313-2 may receive the first amplified time resolved beam ATRB1 from the first amplification stage 313-1. The second amplification stage 313-2 may output a second amplified time resolved beam ATRB2 obtained by further amplifying the first amplified time resolved beam ATRB1. For example, an output power of the second amplification stage 313-2 may be about 100 to 200 [mW]. The second amplification stage 313-2 may have the cladding pumping structure.

The third amplification stage 313-3 may receive the second amplified time resolved beam ATRB2 from the second amplification stage 313-2. The third amplification stage 313-3 may output the second incident beam IB2 obtained by further amplifying the second amplified time resolved beam ATRB2 to the sample SP. For example, an output power of the third amplification stage 313-3 may be about 1 to 3 [W]. The third amplification stage 313-3 may have the cladding pumping structure.

Figure 11A:
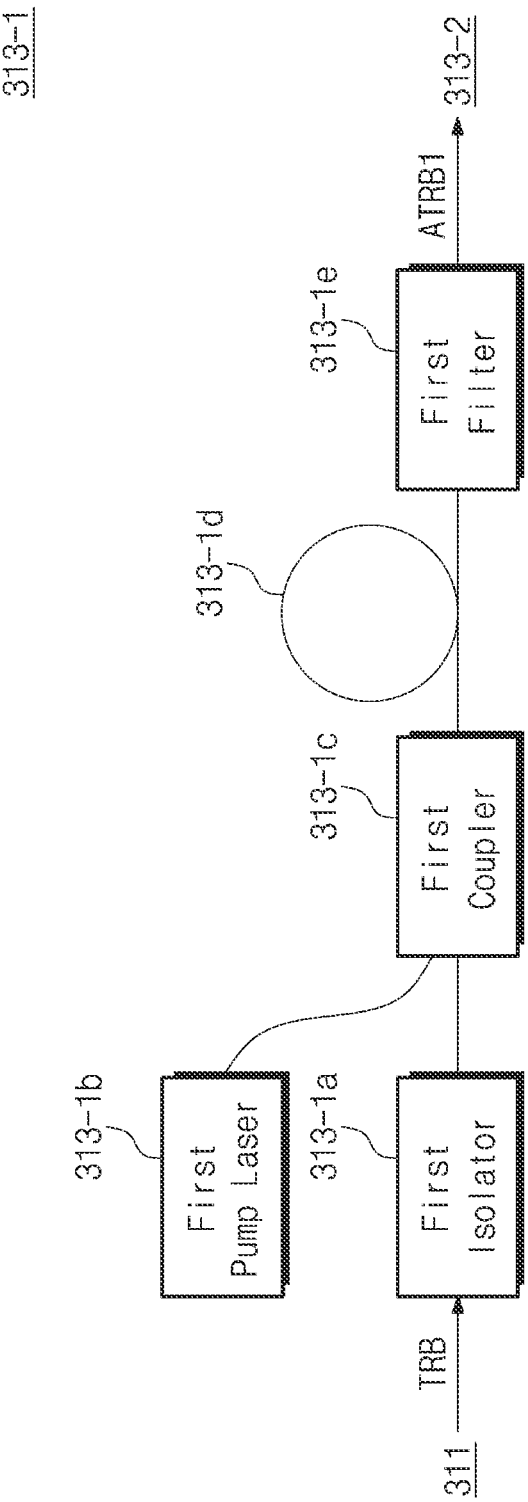
FIG. 11A is a block diagram exemplarily describing a first amplification stage of FIG. 10.

FIG. 11A is a block diagram exemplarily describing a first amplification stage of FIG. 10. Referring to FIG. 11A, the first amplification stage 313-1 may include a first isolator 313-1a, a first pump laser 313-1b, a first coupler 313-1c, a first optical fiber 313-1d, and a first filter 313-1e.

The first isolator 313-1a may be an optical isolator that increases the output of the time resolved beam TRB by blocking light reflected back to the light source. The first pump laser 313-1b may be a light source that outputs a pump laser beam for optically pumping a gain medium. The first coupler 313-1c may be a device that couples the time resolved beam TRB and the pump laser beam. The first optical fiber 313-1d may be an optical fiber doped with a rare earth. The first filter 313-1e may be a filter that passes the laser beam corresponding to a wavelength of the time resolved beam TRB and blocks noise of another wavelength.

According to an embodiment of the inventive concept, the first amplification stage 313-1 may be provided that amplifies the time resolved beam TRB, based on the pump laser beam output from the first pump laser 313-1b to output the first amplified time resolved beam ATRB1. The first amplified time resolved beam ATRB1 may be a laser beam having a higher intensity than the time resolved beam TRB.

In an exemplary embodiment, the second amplification stage 313-2 may have a structure similar to the first amplification stage 313-1. For example, the second amplification stage 313-2 may include a second isolator, a second pump laser, a second coupler, a second optical fiber, and a second filter. In this case, the second coupler may couple the first amplified time resolved beam ATRB1 and the pump laser beam such that the pump laser output from the second pump laser is launched to a cladding of the optical fiber.

In an exemplary embodiment, the second amplification stage 313-2 may further amplify the first amplified time resolved beam ATRB1, based on the pump laser beam output from the second pump laser to output the second amplified time resolved beam ATRB2. The second amplified time resolved beam ATRB2 may be a laser beam having a higher intensity than the first amplified time resolved beam ATRB1.

Figure 11B:
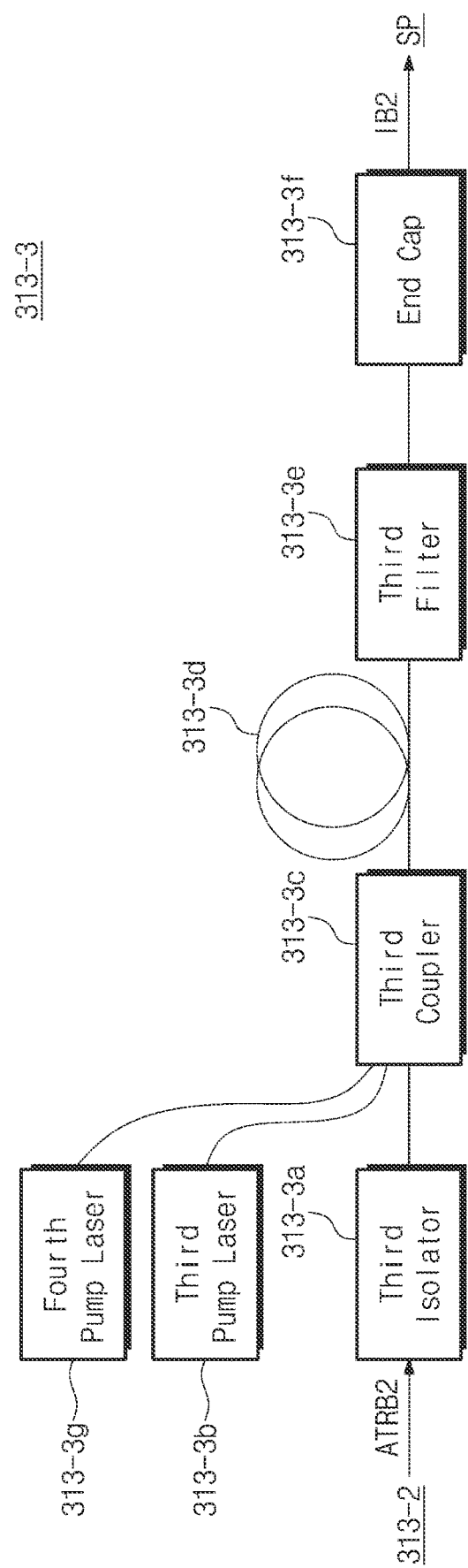
FIG. 11B is a block diagram exemplarily describing a third amplification stage of FIG. 10.

FIG. 11B is a block diagram exemplarily describing a third amplification stage of FIG. 10. Referring to FIG. 11B, the third amplification stage 313-3 may include a third isolator 313-3a, a third pump laser 313-3b, a third coupler 313-3c, a third optical fiber 313-3d, a third filter 313-3e, an end cap 313-3f, and a fourth pump laser 313-3g. Since some components 313-3a to 313-3e of the third amplification stage 313-3 are similar to some of the components 313-1a to 313-1e of the first amplification stage 313-1 of FIG. 11A, detailed descriptions thereof will be omitted.

The fourth pump laser 313-3g may be a light source that outputs the pump laser beam for optically pumping the gain medium. The third coupler 313-3c may be a device that couples the second amplified time resolved beam ATRB2, the pump laser beam output from the third pump laser 313-3b, and the pump laser beam output from the fourth pump laser 313-3g. That is, the third amplification stage 313-3 may include a plurality of pump lasers 313-3b and 313-3g. Accordingly, the third amplification stage 313-3 may have a high amplification gain.

The end cap 313-3f may be a device that emits the laser beam output from the third filter 313-3e. The second incident beam IB2 output from the end cap 313-3f may be irradiated to the sample SP.

According to an embodiment of the inventive concept, based on the pump laser beam output from the third pump laser 313-3b and the pump laser beam output from the fourth pump laser 313-3g, the second incident beam IB2 obtained by further amplifying the second amplified time resolved beam ATRB2 may be output. The second incident beam IB2 may be a laser beam having a higher intensity than the second amplified time resolved beam ATRB2.

Figure 12:
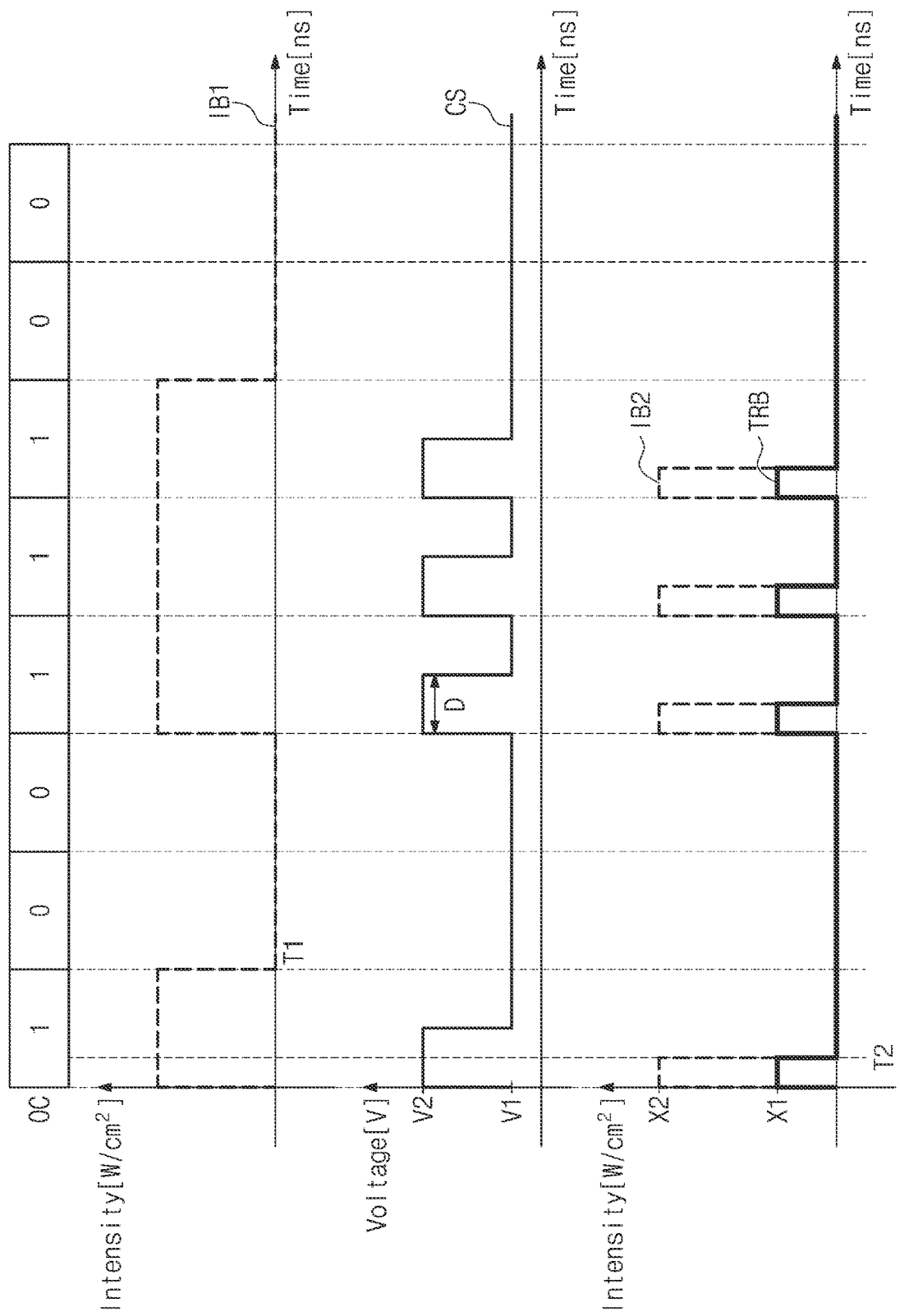
FIG. 12 is a graph illustrating signals generated by a laser irradiation device of FIG. 8.

FIG. 12 is a graph illustrating signals generated by a laser irradiation device of FIG. 8. Referring to FIG. 12, a series of bits included in the orthogonal code OC, a waveform of the control signal CS, a waveform of the time resolved beam TRB, and a waveform of the second incident beam IB2 are illustrated.

In addition, to clearly describe characteristics of the second incident beam IB2, the waveform of the first incident beam IB1 generated by the laser irradiation device of FIG. 5 is also illustrated. Since characteristics of the orthogonal code OC and the first incident beam IB1 are similar to the characteristics of the orthogonal code OC and the first incident beam IB1 described in FIG. 6, detailed descriptions thereof will be omitted.

The control signal CS may be a return-to-zero signal generated based on the orthogonal code. The control signal CS may be an electric signal. The control signal generator 311-1 of FIG. 9 may include information associated with the width and duty ratio 'D' of a section corresponding to a specific bit included in the orthogonal code. For example, in the control signal CS, the width of the section corresponding to the specific bit included in the orthogonal code may be the first time T1. The duty ratio D of the control signal CS may be '0.5'.

In an exemplary embodiment, the control signal CS may have a pulse in the section corresponding to a bit having the value of '1' among bits included in the orthogonal code OC. For example, the control signal CS may have a second voltage V2 for 0.5T1 [ns] in the section corresponding to a bit having the value of '1', and then may have a first voltage V1 for 0.5T1 [ns]. The second voltage V2 may be greater than the first voltage V1. That is, the control signal CS may be the return-to-zero signal having the first voltage V1 after having the second voltage V2 for a specific time.

In an exemplary embodiment, the control signal CS may maintain a unchanged value in a section corresponding to a bit having the value of '0' among bits included in the orthogonal code OC. For example, the control signal CS may maintain the first voltage V1 in the section corresponding to a bit having the value of '0'.

In an exemplary embodiment, the control signal CS may be a signal having a voltage that varies based on values of bits included in the orthogonal code OC. In more detail, the control signal CS may maintain the first voltage V1 in the section corresponding to a bit having the value of '0' among the series of bits of the orthogonal code OC. The control signal CS may have the first voltage V1 after having the second voltage V2 higher than the first voltage V1 in the section corresponding to a bit having the value of '1' among the series of bits of the orthogonal code OC.

The time resolved beam TRB may include the pulsed laser beam that is generated by the main oscillator 311 of FIG. 8, based on the control signal CS. The light source of the main oscillator may have time resolved width information. For example, the time resolved beam TRB may include the pulsed laser beam that is generated in response to a rising edge of the pulse included in the control signal CS. The width of the pulse may be determined as a second time T2, based on the time resolved width information.

That is, the time resolved beam TRB may include the pulsed laser beam in the section corresponding to a bit having the value of '1' among the bits included in the orthogonal code OC. The time resolved beam TRB may not include the pulsed laser beam in the section corresponding to a bit having the value of '0' among the bits included in the orthogonal code OC.

The second incident beam IB2 may be the laser beam obtained by amplifying the time resolved beam TRB. For example, the time resolved beam TRB may have a first intensity X1. The second incident beam IB2 may have a second intensity X2. The second intensity X2 may be greater than the first intensity X1. That is, the second incident beam IB2 may be a laser beam having the same pulse width as the time resolved beam TRB and having a higher intensity than the time resolved beam TRB.

In an exemplary embodiment, the second incident beam IB2 may be a laser beam having a narrower pulse width than the first incident beam IB1. In more detail, the light source that outputs the time resolved beam TRB may output a laser beam including the pulsed laser beam having a higher frequency than the modulator that outputs the first incident beam IB1. Accordingly, the second time T2, which is the pulse width per bit of the second incident beam IB2, may be less than the first time T1, which is the pulse width per bit of the first incident beam IB1.

Figure 13:
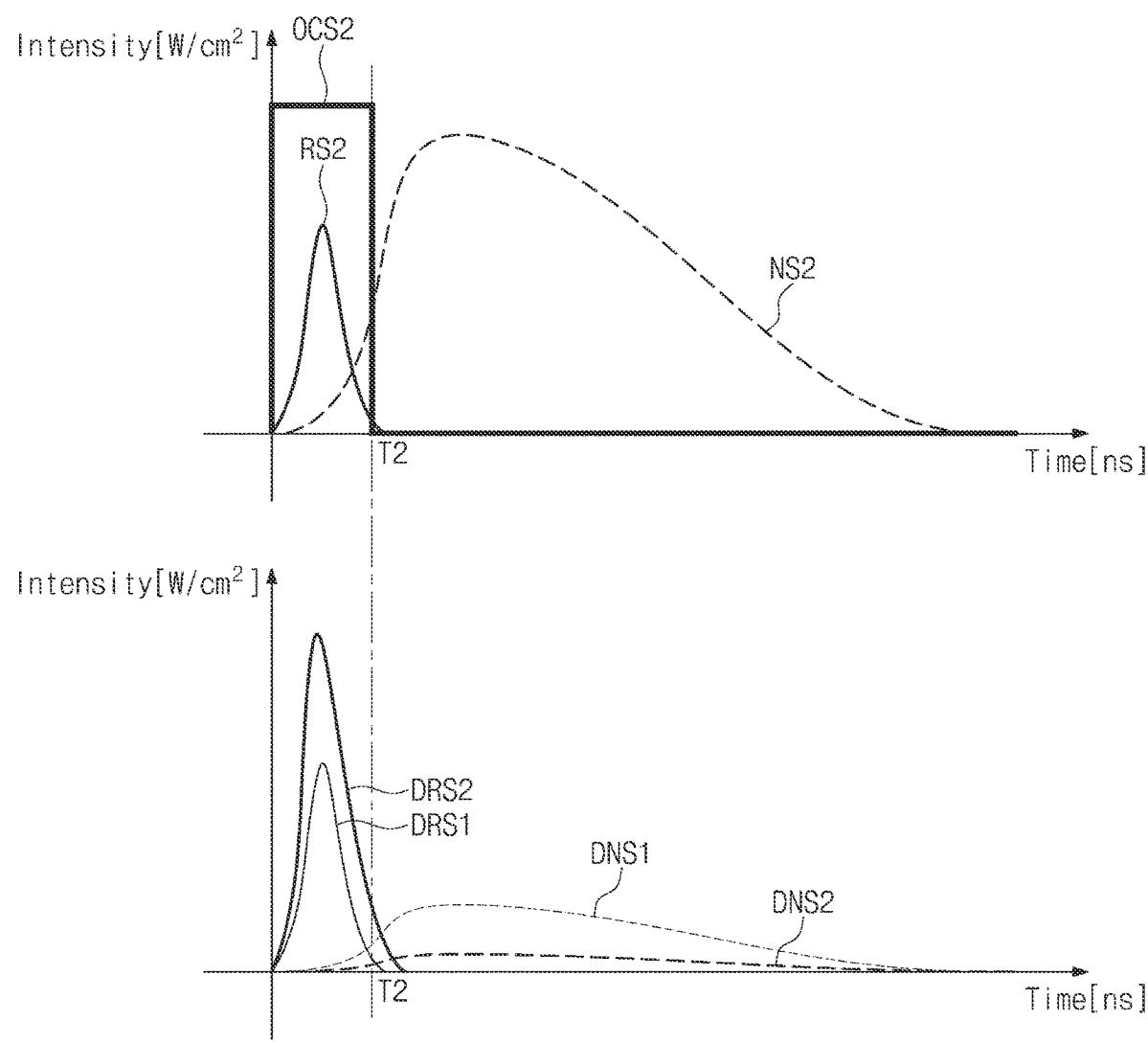
FIG. 13 is a graph illustrating signals processed by a detector of FIG. 8.

FIG. 13 is a graph illustrating signals processed by a detector of FIG. 8. Referring to FIGS. 8 and 13, a second Raman signal RS2 and a second noise signal NS2 that are included in a second detection signal DS2 are illustrated. In addition, a second demodulated Raman signal DRS2 and a second removed noise signal DNS2 that are included in a second demodulated detection signal DDS2 are illustrated.

In addition, to clearly describe characteristics of the second demodulated Raman signal DRS2 and the second removed noise signal DNS2, the first demodulated Raman signal DRS1 and the first removed noise signal DNS1 of FIG. 7 are also illustrated. Since the characteristics of the second Raman signal RS2 and the second noise signal NS2 are similar to the characteristics of the first Raman signal RS1 and the first noise signal NS1 of FIG. 7, detailed descriptions thereof will be omitted.

In an exemplary embodiment, the demodulator 323 may restore the second Raman signal RS2 by calculating an autocorrelation relationship, based on the correlation between the second orthogonal code signal OCS2 and the second Raman signal RS2, and may obtain the second demodulated Raman signal DRS2. The demodulator 323 may obtain the second removed noise signal DNS2 by reducing the second noise signal NS2, based on the correlation between the second orthogonal code signal OCS2 and the second noise signal NS2.

In an exemplary embodiment, as the frequency of the laser beam irradiated to the sample SP and the frequency of a signal used for demodulation increase, a Raman signal having a high intensity may be obtained. For example, the second time T2, which is the pulse width of the second orthogonal code signal OCS2, may be less than the first time T1, which is the pulse width of the first orthogonal code signal OCS1 of FIG. 7. The second demodulated Raman signal DRS2 may be a signal having a higher intensity than the first demodulated Raman signal DRS1.

In an exemplary embodiment, as the frequency of the laser beam irradiated to the sample SP and the frequency of the signal used for demodulation increase, a noise signal having a low intensity may be obtained. For example, the second time T2, which is the pulse width of the second orthogonal code signal OCS2, may be less than the first time T1, which is the pulse width of the first orthogonal code signal OCS1 of FIG. 7. The second removed noise signal DNS2 may be a signal having a lower intensity than the first removed noise signal DNS1.

In an exemplary embodiment, the second time T2, which is the pulse width of the second orthogonal code signal OCS2, may be longer than the lifetime of the second Raman signal RS2 and shorter than the lifetime of the second noise signal NS2.

As described above, according to an embodiment of the inventive concept, by irradiating the second incident beam IB2 including the pulsed laser beam having the high modulation frequency to the sample SP, and by demodulating the second Raman signal RS2 and the second detection signal DS2 with the second orthogonal code signal OCS2 having the high modulation frequency, the spectroscopic apparatus 300 may be provided that has an improved signal-to-noise ratio of the second demodulated Raman signal DRS2 and the second removed noise signal DNS2

Figure 14:
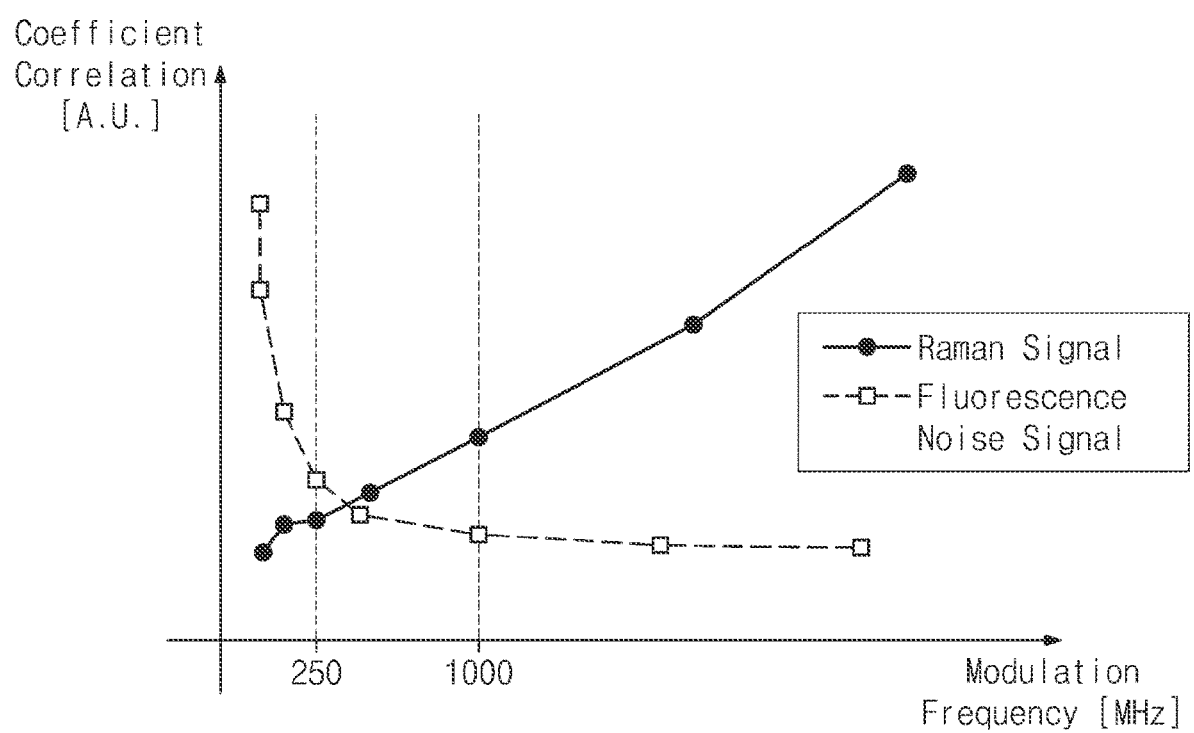
FIG. 14 is a graph illustrating correlation coefficients depending on modulation frequencies of signals processed by the detector of FIG. 8.

FIG. 14 is a graph illustrating correlation coefficients depending on modulation frequencies of signals processed by the detector of FIG. 8. Referring to FIG. 14, correlation coefficients of a Raman signal and a fluorescence noise signal restored by a demodulator depending on a modulation frequency are exemplarily illustrated.

For example, a modulation frequency on a horizontal axis may mean a frequency at which the continuous wave signal CW of FIG. 5 is modulated by the modulator 212 or a reciprocal of the pulse width of the time resolved beam TRB output from the light source 311-3 of FIG. 9. A correlation coefficient on a vertical axis may mean a correlation coefficient with the first orthogonal code signal OCS1 associated with each of the first Raman signal RS1 and the first noise signal NS1 of FIG. 7 or a correlation coefficient with the second orthogonal code signal OCS2 associated with each of the second Raman signal RS2 and the second noise signal NS2 of FIG. 13. The correlation coefficient may mean a value obtained by dividing the covariance between variables by each standard deviation.

In an exemplary embodiment, as the modulation frequency of the spectroscopic apparatus increases, the signal-to-noise ratio of the Raman signal restored by the demodulator and the fluorescence noise signal may be improved. Molecular information of the sample that is analyzed based on the Raman signal having an improved signal-to-noise ratio may have high accuracy and resolution.

For example, a correlation coefficient of the Raman signal at a modulation frequency of 1000 [MHz] may be greater than a correlation coefficient of the Raman signal at a modulation frequency of 250 [MHz]. A correlation coefficient of the fluorescence noise signal at a modulation frequency of 1000 [MHz] may be less than that of the fluorescence noise signal at a modulation frequency of 250 [MHz]. That is, the signal-to-noise ratio of the Raman signal and the fluorescence noise signal at a modulation frequency of 1000 [MHz] may be greater than that of the Raman signal and the fluorescence noise signal at a modulation frequency of 250 [MHz].

FIG. 15 is a flowchart illustrating a spectroscopic method for restoring a Raman signal according to an embodiment of the inventive concept. Referring to FIG. 15, a spectroscopic method of analyzing the sample depending on a Raman spectroscopic method is illustrated by way of example. The spectroscopic apparatus used in the spectroscopic method may include a laser irradiation device and a detector.

In step S310, an orthogonal code may be generated. The orthogonal code may be a code including a series of bits that are mathematically orthogonal to other codes. The orthogonal code may synchronize the laser irradiation device and the detector.

In step S320, a control signal may be generated based on the orthogonal code. The control signal may have a section corresponding to a bit included in the orthogonal code. A pulse may be obtained based on the value of the bit in the corresponding section. In an exemplary embodiment, in a section corresponding to a bit having the value of '1', the control signal may have a pulse waveform. In a section corresponding to a bit having the value of '0', the control signal may maintain a unchanged value.

In step S330, a time resolved laser beam generated based on the control signal may be output. In an exemplary embodiment, the time resolved laser beam may include a pulsed laser beam generated using a rising edge of a pulse included in the control signal as a trigger. In an exemplary embodiment, the time resolved laser beam may include a pulsed laser beam generated using a falling edge of a pulse included in the control signal as the trigger. The pulse width of the time resolved laser beam may be determined based on time resolved width information included in a light source that outputs the time resolved laser beam.

In step S340, an incident beam obtained by amplifying the time resolved laser beam may be irradiated to the sample. In an exemplary embodiment, the time resolved laser beam may include a pulsed laser beam having a narrow pulse width and high intensity. The time resolved laser beam may be amplified through a power amplifier. The amplified time resolved laser beam may be irradiated to the sample.

In step S350, a detection signal may be received from the sample. The detection signal may be a signal generated from the sample to which the incident beam is irradiated. The detection signal may include a Raman signal and a noise signal. The Raman signal may include molecular information of the sample. The Raman signal may have a lower intensity than the noise signal. The Raman signal may be measured with temporal priority over the noise signal.

In step S360, the Raman signal may be demodulated based on a correlation with the orthogonal code. In more detail, an orthogonal code signal synchronized with the incident beam may be generated based on the orthogonal code. The orthogonal code signal may be an electrical signal having the same waveform as the incident beam.

In an exemplary embodiment, the Raman signal may be restored and the noise signal may be removed, based on the correlation between the orthogonal code signal and the detection signal. In this case, as the intensity of the Raman signal increases and the intensity of the noise signal decreases, the signal-to-noise ratio of the demodulated Raman signal may be remarkably improved.

As described above, according to an embodiment of the inventive concept, a spectroscopic method may be provided that irradiates an incident beam including a high modulation frequency pulsed laser beam using a pulse of a control signal generated based on an orthogonal code as a trigger. In addition, a spectroscopic method may be provided that demodulates a Raman signal, based on a correlation with the orthogonal code signal having the same waveform as the incident beam.

The contents described above are specific embodiments for implementing the inventive concept. The inventive concept may include not only the embodiments described above but also embodiments in which a design is simply or easily capable of being changed. In addition, the inventive concept may also include technologies easily changed to be implemented using embodiments. Therefore, the scope of the inventive concept is not limited to the described embodiments but should be defined by the equivalents of the claims as well as the claims to be described later.

INDUSTRIAL APPLICABILITY

The inventive concept relates to a spectroscopic apparatus and a spectroscopic method. In more detail, the inventive concept may be used in a spectroscopic apparatus and a spectroscopic method that analyze a bio-signal using a time resolved coding.

The invention claimed is:

1. A spectroscopic apparatus comprising:
a laser irradiation device configured to receive an orthogonal code including a series of bits each having a first value or a second value, to generate a control signal having a pulse that has a width shorter than a width of a bit section in the bit section corresponding to a bit having the first value among the series of bits, to generate a pulsed laser beam having a pulse width shorter than the bit section using the pulse included in the control signal as a trigger, and to irradiate an incident beam including the generated pulsed laser beam to a sample; and
a detector configured to receive a detection signal generated from the sample to which the incident beam is irradiated and the orthogonal code, to generate an orthogonal code signal of the same waveform as that of the incident beam, based on the orthogonal code, and to demodulate a Raman signal, based on a correlation between the generated orthogonal code signal and the Raman signal included in the detection signal.

2. The spectroscopic apparatus of claim 1, wherein the control signal has a first voltage or a second voltage greater than the first voltage, has the first voltage after having the second voltage in the bit section corresponding to the bit having the first value among the series of bits, and maintains the first voltage in another bit section corresponding to the bit having the second value among the series of bits.

3. The spectroscopic apparatus of claim 1, wherein the laser irradiation device is further configured to generate the pulsed laser beam using a rising edge of the pulse included in the control signal as the trigger.

4. The spectroscopic apparatus of claim 1, wherein the laser irradiation device is further configured to generate the pulsed laser beam using a falling edge of the pulse included in the control signal as the trigger.

5. The spectroscopic apparatus of claim 1, wherein the laser irradiation device includes:
a main oscillator configured to receive the orthogonal code, and to output a time resolved beam including the pulsed laser beam; and
a power amplifier configured to receive the time resolved beam, and to amplify the time resolved beam to irradiate the incident beam to the sample.

6. The spectroscopic apparatus of claim 5, wherein the main oscillator includes:
a control signal generator configured to receive the orthogonal code and output the control signal, based on the received orthogonal code;
a controller configured to receive the control signal and output a trigger signal for generating the pulsed laser beam, based on the control signal; and
a light source configured to receive the trigger signal, to include time resolved width information for determining the pulse width of the pulsed laser beam, and to output the time resolved beam, based on the received trigger signal and the time resolved width information.

7. The spectroscopic apparatus of claim 5, wherein the power amplifier includes an isolator configured to receive the time resolved beam and to block light reflected back to the light source.

8. The spectroscopic apparatus of claim 5, wherein the power amplifier includes:
   a first pump laser configured to output a first pump laser beam for optically pumping a gain medium; and
   a coupler configured to couple the time resolved beam and the first pump laser beam.

9. The spectroscopic apparatus of claim 8, wherein the power amplifier further includes a second pump laser configured to output a second pump laser beam for optically pumping the gain medium, and
   wherein the coupler is further configured to couple the time resolved beam, the first pump laser beam, and the second pump laser beam.

10. The spectroscopic apparatus of claim 5, wherein the power amplifier includes a filter configured to pass a laser beam corresponding to a wavelength of the time resolved beam and to block noise.

11. The spectroscopic apparatus of claim 5, wherein the power amplifier includes:
    a first amplification stage configured to receive the time resolved beam, and to amplify the received time resolved beam to output a first amplified time resolved beam;
    a second amplification stage configured to receive the first amplified time resolved beam, and to output a second amplified time resolved beam in which the first amplified time resolved beam is further amplified; and
    a third amplification stage configured to receive the second amplified time resolved beam, and to irradiate the incident beam in which the second amplified time resolved beam is further amplified to the sample.

12. A spectroscopic method comprising:
    generating an orthogonal code including a series of bits each having a first value or a second value;
    generating a control signal having a pulse that has a width shorter than a width of a bit section in the bit section corresponding to a bit having the first value among the series of bits;
    generating a pulsed laser beam having a pulse width shorter than the bit section using the pulse included in the control signal as a trigger, and irradiating an incident beam including the generated pulsed laser beam to a sample;
    receiving a detection signal output from the sample to which the incident beam is irradiated;
    generating an orthogonal code signal of the same waveform as that of the incident beam, based on the orthogonal code, and demodulating a Raman signal by calculating an autocorrelation coefficient, based on a correlation between the orthogonal code signal and the Raman signal included in the detection signal.

13. The spectroscopic method of claim 12, wherein the detection signal includes:
    a Raman signal having a first intensity and being received at a first time; and
    a noise signal having a second intensity greater than the first intensity and being received at a second time later than the first time.

14. The spectroscopic method of claim 13, wherein the demodulating of the Raman signal further includes removing the noise signal, based on a correlation between the orthogonal code signal and the noise signal, and
    wherein an intensity of the demodulated Raman signal is greater than an intensity of the removed noise signal.

15. The spectroscopic method of claim 12, wherein the detection signal includes the Raman signal having a first lifetime and a noise signal having a second lifetime longer than the first lifetime, and
    wherein the pulse width of the pulsed laser beam is longer than the first lifetime and shorter than the second lifetime.

* * * * *